(12) United States Patent
Uhr et al.

(10) Patent No.: US 6,531,496 B1
(45) Date of Patent: Mar. 11, 2003

(54) O-ARYL DITHIAZOLE DIOXIDES

(75) Inventors: Hermann Uhr, Leverkusen (DE); Christiane Boie, Leichlingen (DE); Heiko Rieck, Langenfeld (DE); Bernd-Wieland Krüger, Bergisch Gladbach (DE); Ulrich Heinemann, Leichlingen (DE); Robert Markert, Köln (DE); Martin Vaupel, Leichlingen (DE); Martin Kugler, Leichlingen (DE); Klaus Stenzel, Düsseldorf (DE); Ulrike Wachendorff-Neumann, Neuwied (DE); Astrid Mauler-Machnik, Leichlingen (DE); Karl-Heinz Kuck, Langenfeld (DE); Peter Lösel, Leverkusen (DE); Shinichi Narabu, Yuki (JP)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/958,552

(22) PCT Filed: Apr. 10, 2000

(86) PCT No.: PCT/EP00/03160

§ 371 (c)(1),
(2), (4) Date: Jan. 22, 2002

(87) PCT Pub. No.: WO00/64881

PCT Pub. Date: Nov. 2, 2000

(30) Foreign Application Priority Data

Apr. 22, 1999 (DE) .......................................... 199 18 294

(51) Int. Cl.⁷ ........................ C07D 285/01; A01N 43/82
(52) U.S. Cl. ............................. 514/360; 544/5; 548/123
(58) Field of Search ............................. 548/123; 544/5; 514/360

(56) References Cited

U.S. PATENT DOCUMENTS 3,345,374 A   10/1967   Dickoré et al. .......... 260/294.8

FOREIGN PATENT DOCUMENTS

| DE | 19 545 635 | 6/1997 |
| WO | 98/29400 | 7/1998 |
| WO | 98/52945 | 11/1998 |

OTHER PUBLICATIONS

*K. Nakahashi et al.: Bull. Chem. Soc. Japan, Bd. 45, Nr. 10, Oct. 1972, Seiten 3217–8 XP002076372.

*K. Hasegawa et al.: Bull. Chem. Soc. Japan, Bd. 45, Nr. 5, May 1972, Seiten 1567–8 XP000915288.

*Primary Examiner*—Robert Gerstl
(74) *Attorney, Agent, or Firm*—Richard E.L. Henderson; Joseph C. Gil

(57) ABSTRACT

The invention relates to new O-aryldithiazole dioxides, to two processes for their preparation, and to their use as pesticides in crop protection and in the protection of materials.

20 Claims, No Drawings

O-ARYL DITHIAZOLE DIOXIDES

FIELD OF THE INVENTION

The invention relates to new O-aryldithiazole dioxides, to two processes for their preparation, and to their use as pesticides in crop protection and in the protection of materials.

BACKGROUND OF THE INVENTION

Certain aryldithiazole dioxides with a similar substitution pattern and their action against organisms which are harmful to plants and materials have already been disclosed (cf. DE-19545635 and WO98-29400). However, the action of these state-of-the-art compounds is not entirely satisfactory in all fields of application, in particular when low application rates and concentrations are used.

DETAILED DESCRIPTION

There have now been found the new compounds of the general formula (I)

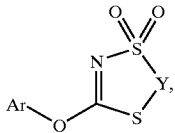

in which
Ar represents substituted or unsubstituted aryl and
Y represents substituted or unsubstituted, straight-chain or branched alkanediyl.

In the definitions, the saturated or unsaturated hydrocarbon chains, such as alkyl, are in each case straight-chain or branched, also when linked to hetero atoms, such as in alkoxy or alkylthio.

Aryl represents aromatic, mono or polycyclic hydrocarbon rings such as, for example, phenyl, naphthyl, anthranyl, phenanthryl, preferably phenyl or naphthyl, in particular phenyl.

Substituents of the present application are to be understood as meaning in particular those where individual preferred ranges are mentioned.

The following are substituents for aryl or for alkanediyl, in particular for aryl: halogen, cyano, thiocyano, nitro, amino, formyl, carbamoyl, thiocarbamoyl, hydrogen, hydroxyl; in each case straight-chain or branched alkyl, cyanoalkyl, hydroxyalkyl, alkoxy, alkoxyalkyl, hydroxyalkoxy, alkylthioalkyl, alkylaminoalkyl, dialkylaminoalkyl, alkylthio, alkylsulphinyl or alkylsulphonyl, each of which has 1 to 8 carbon atoms; in each case straight-chain or branched alkenyl, alkenyloxy or alkenylcarbonyl, each of which has 2 to 6 carbon atoms in the alkenyl moiety and each of which is optionally monosubstituted or disubstituted by cyano, nitro, phenyl, nitrophenyl, dinitrophenyl, alkoxycarbonylamino, phthalimidyl, bis-(alkoxycarbonylamino) or dioxobenzimidazolyl; in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms; in each case straight-chain or branched halogenoalkenyl or halogenoalkenyloxy, each of which has 2 to 6 carbon atoms and 1 to 11 identical or different halogen atoms; in each case straight-chain or branched alkylamino, dialkylamino, alkylcarbonyl, thiocyanoalkylcarbonyl, halogenoalkylcarbonyl (having 1 to 3 halogen atoms), alkoxycarbonyl, alkoxycarbonylazoalkyl, alkylaminocarbonyl, dialkyl-aminocarbonyl or arylalkylaminocarbonyl having 1 to 6 carbon atoms in the respective hydrocarbon chains, or cycloalkylcarbonylamino or cycloalkyl, each of which has 3 to 6 carbon atoms in the cycloalkyl moiety and each of which is optionally monosubstituted to tetrasubstituted by halogen or alkyl having 1 to 4 carbon atoms; cycloalkyl or cycloalkyloxy, each of which has 3 to 6 carbon atoms; phenyl, phenoxy, phenylazo, phenylthio, phenylsulphonyl, phenylcarbonyl, phenylalkylcarbonyl, or phenylalkoxy having 1 to 4 carbon atoms in the alkyl moiety, optionally substituted in each case by halogen, alkyl, phenyl, alkoxy, alkylthio, alkylsulphinyl or alkylsulphonyl having 1 to 4 carbon atoms, halogenoalkyl, halogenoalkoxy, halogenoalkylthio, halogenoalkylsulphinyl or halogenoalkylsulphonyl having 1 to 4 carbon atoms and 1 to 9 halogen atoms, heterocyclyl, heterocyclylalkyl having 1 to 4 carbon atoms in the alkyl moiety, heterocyclyloxy, heterocyclylthio, heterocyclylsulphinyl, heterocyclylsulphonyl, heterocyclylcarbonyl, heterocyclylthiocarbonyl, benzoheterocyclyl, benzoheterocyclylalkyl having 1 to 4 carbon atoms in the alkyl moiety, benzoheterocyclyloxy, benzoheterocyclylthio, benzoheterocyclylsulphinyl, benzoheterocyclylsulphonyl, benzoheterocyclylcarbonyl or benzoheterocyclylthiocarbonyl, each of which has 5 or 6 ring members in the heterocyclyl moiety, in each case optionally substituted by halogen, oxo, alkyl, alkoxy, alkylthio, alkylsulphinyl or alkylsulphonyl having 1 to 4 carbon atoms, halogenoalkyl, halogenoalkoxy, halogenoalkylthio, halogenoalkylsulphinyl or halogenoalkylsulphonyl having 1 to 4 carbon atoms and 1 to 9 halogen atoms or phenyl, or a group

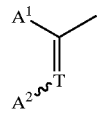

where
T represents CH or nitrogen,
$A^1$ represents hydrogen or alkyl having 1 to 4 carbon atoms, cycloalkyl having 3 to 6 carbon atoms, phenyl, heterocyclyl having 5 or 6 ring members, alkoxycarbonyl having 1 to 4 carbon atoms in the alkyl moiety, benzylaminocarbonyl, benzyloxyaminocarbonyl or aminocarbonyl, and
$A^2$ represents hydroxyl, amino, alkyl, phenyl, benzyl, alkoxy, cyanoalkoxy, benzyloxy, alkylamino, dialkylamino, alkoxycarbonylamino, alkoxycarbonylphenyl, in each case having 1 to 4 carbon atoms in the respective alkyl chains, or alkenyloxy having 2 to 4 carbon atoms.

Halogenoalkyl represents partially or fully halogenated alkyl. In the case of polyhalogenated halogenoalkyl, the halogen atoms can be identical or different. Preferred halogen atoms are fluorine and chlorine, and in particular fluorine. If the halogenoalkyl has additionally attached to it further substituents, the maximum number of halogen atoms which is possible is reduced to the free valencies which remain.

Halogen generally represents fluorine, chlorine, bromine or iodine, preferably fluorine, chlorine or bromine, in particular fluorine or chlorine.

Heterocyclyl represents saturated or unsaturated, and also aromatic, cyclic compounds in which at least one ring member is a hetero atom, i.e. an atom other than carbon. If the ring contains more than one hetero atom, these may be identical or different. Preferred hetero atoms are oxygen, nitrogen or sulphur. If the ring contains more than one oxygen atom, these are not adjacent to each other. If appropriate, the cyclic compounds together with further carbocyclic or heterocyclic, fused or bridged rings form a polycyclic ring system. A polycyclic ring system can be linked via the heterocyclic ring or a fused carbocyclic ring. Preferred are mono- or bicyclic ring systems, in particular mono- or bicyclic aromatic ring systems.

Furthermore, it has been found that the new compounds of the general formula (I) are obtained (process a) when dithiazole dioxides of the general formula (II)

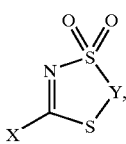
(II)

in which
Y is as stated above and
X represents halogen, alkyl- or arylsulphonyl
are reacted with phenols of the general formula (III)

Ar—OH (III)

in which
Ar is as stated above and
if appropriate in the presence of a diluent, if appropriate in the presence of an acid acceptor and if appropriate in the presence of a catalyst.

Finally, it has been found that the new compounds of the general formula (I) have a very potent fungicidal and insecticidal action.

If appropriate, the compounds according to the invention can exist as mixtures of various isomeric forms which are possible, in particular in the form of stereoisomers, such as, for example, E- and Z-isomers, or optical isomers. All of the E- and Z-isomers, the individual enantiomers, the racemates, and any mixtures of these isomers are claimed.

Subject-matter of the invention are preferably compounds of the formula (I-a)

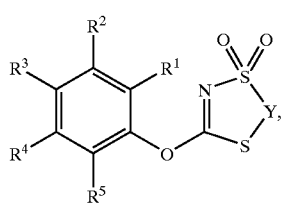
(I-a)

in which
$R^1$, $R^2$, $R^3$, $R^4$ and $R^5$ are identical or different and independently of one another represent the following substituents:
halogen, cyano, thiocyano, nitro, amino, formyl, carbamoyl, thiocarbamoyl, hydrogen, hydroxyl;

in each case straight-chain or branched alkyl, cyanoalkyl, hydroxyalkyl, alkoxy, alkoxyalkyl, hydroxyalkoxy, alkylthioalkyl, alkylaminoalkyl, dialkylaminoalkyl, alkylthio, alkylsulphinyl or alkylsulphonyl, each of which has 1 to 8 carbon atoms;

in each case straight-chain or branched alkenyl, alkenyloxy or alkenylcarbonyl, each of which has 2 to 6 carbon atoms in the alkenyl moiety and each of which is optionally monosubstituted or disubstituted by cyano, nitro, phenyl, nitrophenyl, dinitrophenyl, alkoxycarbonylamino, phthalimidyl, bis-(alkoxycarbonylamino) or dioxobenzimidazolyl;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

in each case straight-chain or branched halogenoalkenyl or halogenoalkenyloxy, each of which has 2 to 6 carbon atoms and 1 to 11 identical or different halogen atoms;

in each case straight-chain or branched alkylamino, dialkylamino, alkylcarbonyl, thiocyanoalkylcarbonyl, halogenoalkylcarbonyl (having 1 to 3 halogen atoms), alkoxycarbonyl, alkoxycarbonylazoalkyl, alkylaminocarbonyl, dialkylaminocarbonyl or arylalkylaminocarbonyl having 1 to 6 carbon atoms in the respective hydrocarbon chains, or cycloalkylcarbonylamino or cycloalkyl having 3 to 6 carbon atoms in the cycloalkyl moiety, each of which is optionally monosubstituted to tetrasubstituted by halogen or halkyl having 1 to 4 carbon atoms; cycloalkyl or cycloalkyloxy, each of which has 3 to 6 carbon atoms; phenyl, phenoxy, phenylazo, phenylthio, phenylsulphonyl, phenylcarbonyl, phenylalkylcarbonyl, or phenylalkoxy having 1 to 4 carbon atoms in the alkyl moiety, in each case optionally substituted by halogen, alkyl, phenyl, alkoxy, alkylthio, alkylsulphinyl or alkylsulphonyl having 1 to 4 carbon atoms, halogenoalkyl, halogenoalkoxy, halogenoalkylthio, halogenoalkylsulphinyl or halogenoalkylsulphonyl having 1 to 4 carbon atoms and 1 to 9 halogen atoms, heterocyclyl, heterocyclylalkyl having 1 to 4 carbon atoms in the alkyl moiety, heterocyclyloxy, heterocyclylthio, heterocyclylsulphinyl, heterocyclylsulphonyl, heterocyclylcarbonyl, heterocyclylthiocarbonyl, benzoheterocyclyl, benzoheterocyclylalkyl having 1 to 4 carbon atoms in the alkyl moiety, benzoheterocyclyloxy, benzoheterocyclylthio, benzoheterocyclylsulphinyl, benzoheterocyclylsulphonyl, benzoheterocyclylcarbonyl or benzoheterocyclylthiocarbonyl, each of which has 5 or 6 ring members in the heterocyclyl moiety, in each case optionally substituted by halogen, oxo, alkyl, alkoxy, alkylthio, alkylsulphinyl or alkylsulphonyl having 1 to 4 carbon atoms, halogenoalkyl, halogenoalkoxy, halogenoalkylthio, halogenoalkylsulphinyl or halogenoalkylsulphonyl having 1 to 4 carbon atoms and 1 to 9 halogen atoms or phenyl, or a group

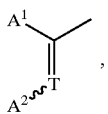

where

T represents CH or nitrogen,

A¹ represents hydrogen or alkyl having 1 to 4 carbon atoms, cycloalkyl having 3 to 6 carbon atoms, phenyl, heterocyclyl having 5 or 6 ring members, alkoxycarbonyl having 1 to 4 carbon atoms in the alkyl moiety, benzylaminocarbonyl, benzyloxyaminocarbonyl or aminocarbonyl, A² represents hydroxyl, amino, alkyl, phenyl, benzyl, alkoxy, cyanoalkoxy, benzyloxy, alkylamino, dialkylamino, alkoxycarbonylamino, alkoxycarbonylphenyl, each of which has 1 to 4 carbon atoms in the respective alkyl chains, or alkenyloxy having 2 to 4 carbon atoms, and Y represents alkylene having 1 to 8 carbon atoms which is optionally monosubstituted or disubstituted by phenyl, the linkage sites of the alkylene chain especially preferably being at the same or at directly adjacent carbon atoms.

Likewise, subject-matter of the invention are preferably compounds of the formula (I-b)

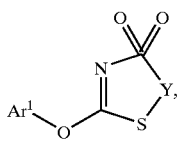

in which

Ar¹ represents one of the following groups:

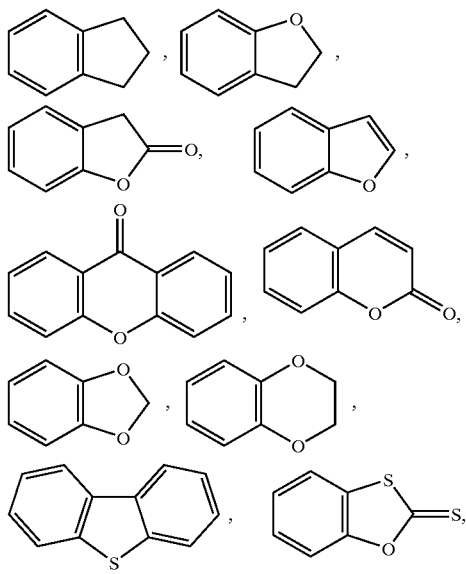

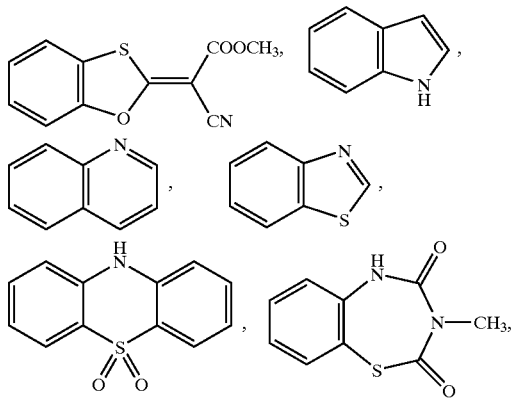

each of which is bonded via the phenyl ring and each of which can, in turn, be monosubstituted to hexasubstituted, the substituents which are possible preferably being selected amongst the following list: halogen, cyano, thiocyano, nitro, amino, formyl, carboxyl, carbamoyl, thiocarbamoyl;
   in each case straight-chain or branched alkyl, alkoxy, alkylthio, alkylsulphinyl or alkylsulphonyl, each of which has 1 to 8 carbon atoms;
   in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;
   in each case straight-chain or branched alkylamino, dialkylamino, alkylcarbonyl, alkoxycarbonyl, alkylaminocarbonyl, dialkylaminocarbonyl or arylalkylaminocarbonyl having 1 to 6 carbon atoms in the respective hydrocarbon chains or cycloalkylcarbonylamino or cycloalkyl having 3 to 6 carbon atoms in the cycloalkyl moiety, in each case monosubstituted to tetrasubstituted by halogen or alkyl having 1 to 4 carbon atoms;
   cycloalkyl or cycloalkyloxy, each of which has 3 to 6 carbon atoms;
   phenyl, phenoxy, phenylthio, phenylsulphonyl, phenylcarbonyl, phenylalkylcarbonyl, or phenylalkoxy having 1 to 4 carbon atoms in the alkyl moiety, in each case optionally substituted by nitro, halogen, alkyl, phenyl, alkoxy, alkylthio, alkylsulphinyl or alkylsulphonyl having 1 to 4 carbon atoms, halogenoalkyl, halogenoalkoxy, halogenoalkylthio, halogenoalkylsulphinyl or halogenoalkylsulphonyl having 1 to 4 carbon atoms and 1 to 9 halogen atoms, and Y represents alkylene having 1 to 8 carbon atoms which is optionally monosubstituted or disubstituted by phenyl, the linkage sites of the alkylene chain especially preferably being at the same or at directly adjacent carbon atoms.

The present application relates in particular to compounds of the formula (I-a), in which
   R¹, R², R³, R⁴ and R⁵ are identical or different and independently of one another represent the following substituents:
      fluorine, chlorine, bromine, cyano, thiocyano, nitro, amino, formyl, carbamoyl, thiocarbamoyl, hydrogen, hydroxyl, methyl, ethyl, n- or i-propyl, n-, i-, s- or t-butyl, methoxymethyl, cyanomethyl, hydroxymethyl, hydroxyethyl, hydroxypropyl, hydroxybutyl, hydroxypentyl, hydroxyhexyl, methoxy, ethoxy, n- or i-propoxy, hydroxyethoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy, vinylcarbonyl, allylcarbonyl, 2-methylallylcarbonyl, propen-1-ylcarbonyl, crotonylcarbonyl, propargylcarbonyl, each of which is optionally monosubstituted or disubstituted by cyano, nitro, phenyl, nitrophenyl, dinitrophenyl, methoxycarbonylamino, phthalimidyl, bis-(methoxycarbonylamino) or dioxobenzimidazolyl; trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, methylcarbonyl, acetyl, propionyl, thiocyanomethylcarbonyl, chloro-t-butylcarbonyl, methoxycarbonyl, ethoxycarbonyl, ethoxycarbonylazomethyl, methylaminocarbonyl, ethylaminocarbonyl, dimethylaminocarbonyl, diethylaminocarbonyl; or cyclopropyl, cyclopropylcarbonylamino, cyclobutyl, cyclopentyl or cyclohexyl, each of which is optionally monosubstituted to tetrasubstituted by chlorine, bromine, methyl or ethyl; cyclopentyl, cyclohexyl, cyclopentyloxy, cyclohexyloxy, cyclohexylcarbonylamino, phenyl, phenoxy, phenylazo, phenylthio, phenylsulphonyl, phenylcarbonyl, benzylcarbonyl or benzyl, each of which is optionally substituted by nitro, fluorine, chlorine, methyl, trifluoromethyl, phenyl or methoxy, dithiazole, dithiazoloxy, oxadiazole, benzofuranyl, benzofuranylcarbonyl, pyridazine, benzoxazole, pyrimidyl, morpholinyl, morpholinylthiocarbonyl, thienyl, imidazolyl, thiadiazolyl, pyridyl, pyridazinone, furyl, piperazinyl, pyrimidylthio, thiazolyl, thiazolylthio, benzazothiepine, dioxazinyl, thiadiazolylsulphonyl, each of which is optionally monosubstituted to trisubstituted by methyl, ethyl, n- or i-propyl, n-, i-, s- or t-butyl, oxo, fluorine, chlorine, bromine, trifluoromethyl or phenyl; or a group

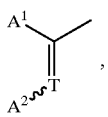

in which

T represents CH or nitrogen, $A^1$ represents hydrogen, methyl, ethyl, n- or i-propyl, n-, i-, s- or t-butyl, cyclopentyl, cyclohexyl, phenyl, dioxazinyl, methoxycarbonyl, ethoxycarbonyl, benzylaminocarbonyl, benzyloxyaminocarbonyl or aminocarbonyl, $A^2$ represents hydroxyl, amino, methyl, ethyl, phenyl, benzyl, methoxy, ethoxy, n- or i-propoxy, n-, i-, s- or t-butoxy, cyanomethoxy, benzyloxy, methylamino, ethylamino, dimethylamino, diethylamino, methoxycarbonylamino, ethoxycarbonylamino, methoxycarbonylphenyl, ethoxycarbonylphenyl or allyloxy, and Y represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally monosubstituted or disubstituted by phenyl.

Likewise, the present application in particular relates to compounds of the formula (I-b) in which $Ar^1$ represents one of the following groups:

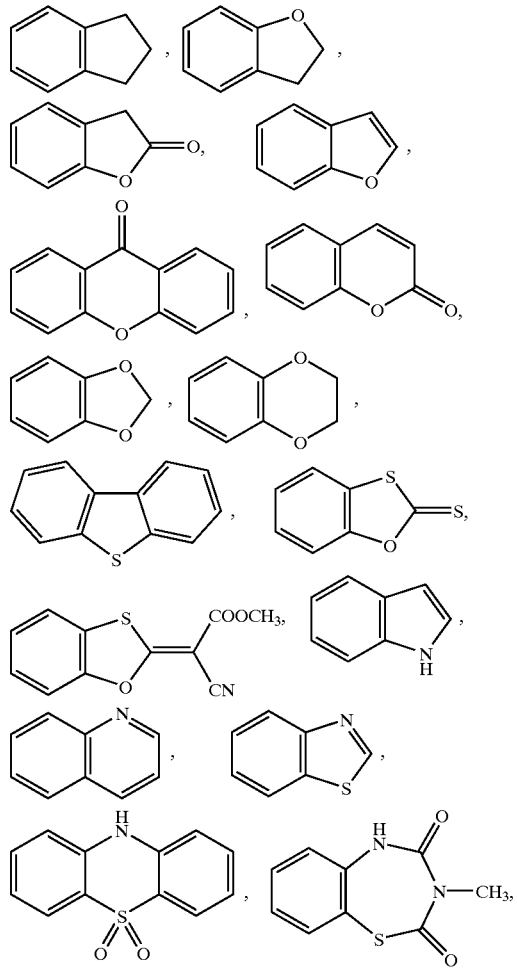

each of which is bonded via the phenyl ring and can, in turn, be monosubstituted to hexasubstituted, the substituents which are possible preferably being selected from amongst the following list:

fluorine, chlorine, bromine, cyano, thiocyano, nitro, amino, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluoro-chloromethoxy, trifluoroethoxy, pentafluoroethoxy, 2-chloro-1,1,2-trifluoro-ethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl; cyclopropyl, cyclobutyl, cyclopentyl or cyclohexyl, each of which is optionally monosubstituted to tetrasubstituted by chlorine, bromine, methyl or ethyl; cyclopentyl, cyclohexyl, cyclopentyloxy, cyclohexyloxy, phenyl, phenoxy, phenylthio, phenylsulphonyl, phenylcarbonyl, benzylcarbonyl or benzyl, each of which is optionally substituted by nitro, fluorine, chlorine, methyl, trifluoromethyl, phenyl or methoxy, and Y represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally monosubstituted or disubstituted by phenyl.

Preferred compounds are those in which $R^2$ represents chlorine, methyl, methoxy, hydroxymethyl, hydroxyethyl, trifluoromethoxy, methylcarbonyl or methoxycarbonyl, in particular hydrogen.

Preferred compounds are those in which $R^3$ represents fluorine, chlorine, trifluoromethyl, methyl, nitro, methoxy, methylcarbonyl or methoxycarbonyl, in particular hydrogen.

Especially preferred compounds are those in which $R^5$ represents hydrogen, chlorine, methyl, methoxy, in particular hydrogen.

Especially preferred compounds are those in which $R^4$ represents halogen, nitro, methoxy, carbonylmethyl, halogenomethyl, methoximinoethyl, in particular hydrogen.

Especially preferred compounds are those of the formula (I) in which

Y represents methylene, 1,2-ethylene, phenyl-substituted 1,2-ethylene, 1,1-ethylene, in particular methylene.

The definitions of radicals stated above in general terms or in preferred ranges apply not only to the end products of the formula (I), but also, correspondingly, to the starting materials or intermediates required in each case for the preparation.

The definitions of radicals stated individually for these radicals in the respective combinations or preferred combinations of radicals are also replaced by any definitions of radicals of other preferred ranges, independently of the particular combination of radicals stated.

Formula (II) provides a general definition of the dithiazole dioxides required as starting materials for carrying out process a) according to the invention for the preparation of the compounds of the formula (I) according to the invention. In this formula (II), Y preferably, or in particular, has the meaning which has already been stated in connection with the description of the compounds of the formula (I) according to the invention as being preferred, or particularly preferred, for Y. X represents halogen, preferably chlorine or bromine, or alkyl- or arylsulphonyl, preferably methyl- or p-tolylsulphonyl.

Some of the starting materials of the formula (II) are known and can be prepared by known methods (compare, for example, WO 98-52945 or Bull. Chem. Soc. Jap. (1972), 45(10), 3217–18). New, and likewise subject-matter of the present invention, are dithiazole dioxides of the formula (II-a)

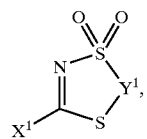

in which $Y^1$ represents methylene or 1,2-ethylene, each of which is monosubstituted or disubstituted by phenyl, or represents 1,1-ethylene, 1,1-, 1,2- or 2,2-propylene, 1,1-, 1,2-, 2,2-, 2,3-butylene or 1,1- or 1,2-(2-methylpropylene), each of which is optionally monosubstituted or disubstituted by phenyl, and $X^1$ represents halogen, preferably chlorine or bromine.

They are obtained (process b) when alkylthiodithiazoles of the general formula (IV)

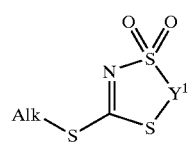

in which $Y^1$ is as stated above and

Alk represents alkyl are reacted with a halogenating agent, preferably a customary chlorinating, brominating or iodinating agent, such as, for example, chlorine, bromine, iodine, sulphuryl chloride, chlorosuccinimide, bromosuccinimide, 1,3-dibromo-5,5-dimethylhydantoin or iodosuccinimide, if appropriate in the presence of a diluent.

Formula (IV) provides a general definition of the alkylthiodithiazole dioxides required as starting materials for carrying out process b) according to the invention for the preparation of the intermediates of the formula (II) according to the invention. In this formula (IV), $Y^1$ preferably, or in particular, has the meaning which has already been mentioned in connection with the description of the compounds of the formula (II) according to the invention as being preferred, or particularly preferred, for $Y^1$. Alk represents alkyl, preferably methyl or ethyl.

Some of the starting materials of the formula (IV) are known and can be prepared by known methods (compared, for example, U.S. Pat. No. 3345374).

Formula (III) provides a general definition of the phenols furthermore required as starting materials for carrying out process a) according to the invention for the preparation of the compounds of the formula (I) according to the invention. In this formula (III), Ar preferably, or in particular, has the meaning which has already been mentioned in connection with the description of the compounds of the formula (I) according to the invention as being preferred, or particularly preferred, for Ar.

The starting materials of the formula (III) are known chemicals for synthesis.

Suitable diluents for carrying out process a) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, tetrachloromethane, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide; sulphones, such as sulpholane; or alcohols, such as tert-butanol.

If appropriate, process a) according to the invention is carried out in the presence of a suitable acid acceptor. Suitable acid acceptors are all customary inorganic or organic bases. These preferably include alkaline earth metal hydrides, alkali metal hydrides, alkaline earth metal hydroxides or alkali metal hydroxides, such as, for example, sodium hydride, potassium tert-butoxide, sodium hydroxide, potassium hydroxide, and also tertiary amines such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process according to the invention, the reaction temperatures can be varied within a substantial range. In general, the process is carried out at temperatures from 0° C. to 150° C., preferably at temperatures from 0° C. to 80° C.

To carry out the process according to the invention for the preparation of the compounds of the formula (I), 1 to 15 mol, preferably 1 to 8 mol, of phenol of the formula (III) are generally employed per mole of the dithiazole of the formula (II).

In general, the processes according to the invention are generally carried out under atmospheric pressure. However, it is also possible to carry out the processes under elevated or reduced pressure, in general between 0.1 bar and 10 bar.

The reaction is carried out and the reaction products are worked up and isolated by generally customary methods (compare also the preparation examples).

The substances according to the invention exhibit a potent microbicidal action and can be employed for controlling undesired microorganisms such as fungi and bacteria in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species such as, for example, *Xanthomonas campestris* pv. oryzae;
Pseudomonas species such as, for example, *Pseudomonas syringae* pv. lachrymans;
Erwinia species such as, for example, *Erwinia amylovora;*
Pythium species such as, for example, *Pythium ultimum;*
Phytophthora species such as, for example, *Phytophthora infestans;*
Pseudoperonospora species such as, for example, *Pseudoperonospora humuli* or *Pseudoperonospora cubensis;*
Plasmopara species such as, for example, *Plasmopara viticola;*
Bremia species such as, for example, *Bremia lactucae;*
Peronospora species such as, for example, *Peronospora pisi* or *P. brassicae;*
Erysiphe species such as, for example, *Erysiphe graminis;*
Sphaerotheca species such as, for example, *Sphaerotheca fuliginea;*
Podosphaera species such as, for example, *Podosphaera leucotricha;*
Venturia species such as, for example, *Venturia inaequalis;*
Pyrenophora species such as, for example, *Pyrenophora teres* or *P. graminea* (conidial form: Drechslera, syn: Helminthosporium);
Cochliobolus species such as, for example, *Cochilobolus sativus* (conidial form: Drechslera, syn: Helminthosporium);
Uromyces species such as, for example, *Uromyces appendiculatus;*
Puccinia species such as, for example, *Puccinia recondita;*
Sclerotinia species such as, for example, *Sclerotinia sclerotiorum;*
Tilletia species such as, for example, *Tilletia caries;*
Ustilago species such as, for example, *Ustilago nuda* or *Ustilago avenae;*
Pellicularia species such as, for example, *Pellicularia sasakii;*
Pyricularia species such as, for example, *Pyricularia oryzae;*
Fusarium species such as, for example, *Fusarium culmorum;*
Botrytis species such as, for example, *Botrytis cinerea;*
Septoria species such as, for example, *Septoria nodorum;*
Leptosphaeria species such as, for example, *Leptosphaeria nodorum;*
Cercospora species such as, for example, *Cercospora canescens;*
Altemaria species such as, for example, *Alternaria brassicae;*
Pseudocercosporella species such as, for example, *Pseudocercosporella herpotrichoides.*

The fact that the active compounds are well tolerated by plants at the concentrations required for controlling plant diseases permits the treatment of aerial plant parts, of propagation stock and seeds, and of the soil.

In this context, the active compounds according to the invention can be employed particularly successfully for controlling diseases in viticulture, fruit production and vegetable production, such as, for example, against Venturia, Phytophtora and Plasmopara species.

Other diseases in viticulture, fruit production and vegetable production, such as, for example, Pythium species, or rice diseases such as, for example, Pyricularia species, are also controlled very successfully.

In the protection of materials, the substances according to the invention can be employed for protecting industrial materials from attack and destruction by undesired microorganisms.

Industrial materials are to be understood as meaning, in the present context, non-live materials which have been produced for use in industry. For example, industrial materials to be protected from microbial change or destruction by active compounds according to the invention can be glues, sizes, paper and board, textiles, leather, wood, paint and plastic articles, cooling lubricants and other materials which can be attacked or broken down by microorganisms. Parts of production plants, for example cooling-water circuits, which may be impaired by the multiplication of microorganisms may also be mentioned within the scope of the materials to be protected. Industrial materials which may be mentioned within the scope of the present invention are preferably glues, sizes, paper and board, leather, wood, paints, cooling lubricants and heat-transfer liquids.

Examples of microorganisms which are capable of bringing about degradation of, or change in, the industrial materials which may be mentioned are bacteria, fungi, yeasts, algae and slime organisms. The active compounds according to the invention preferentially act against fungi, in particular moulds, wood-discolouring and wood-destroying fungi (Basidiomycetes) and against slime organisms and algae.

Examples which may be mentioned are microorganisms of the following genera:
Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Scierophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

Depending on their particular physical and/or chemical properties, the active compounds can be converted into the customary formulations, such as solutions, emulsions, suspensions, powders, foams, pastes, granules, aerosols, microencapsulations in polymer substances and in coating compositions for seeds, and ULV cold and hot mist formulations.

These formulations are produced in the known manner, for example by mixing the active compounds with extenders, that is liquid solvents, liquefied gases under pressure, and/or solid carriers, optionally with the use of surfactants, that is emulsifiers and/or dispersants and/or foam formers. In the case of the use of water as extender, organic solvents can, for example, also be used as cosolvents. The following are mainly suitable as liquid solvents: aromatics such as xylene, toluene or alkylnaphthalene, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, alcohols such as butanol or glycol and their ethers and esters, ketones, such as acetone, methyl ethyl ketone, methyl isobutyl ketone or cyclohexanone, strongly polar solvents such as dimethylformamide and dimethyl sulphoxide, and also water. Liquefied gaseous extenders or carriers are to be understood as meaning liquids which are gaseous at ambient temperature and under atmospheric pressure, for example aerosol propellants, such as halogenohydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly-disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks.

Suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

In general, the formulations comprise between 0.1 and 95 per cent by weight of active compound, preferably between 0.5 and 90%.

The active compounds according to the invention, as such or in their formulations, can also be used as a mixture with known fungicides, bactericides, acaricides, nematicides or insecticides, for example to widen the spectrum of action or to prevent the development of resistance. In many cases, synergistic effects are obtained, that is, the activity of the mixture is greater than the activity of the individual components.

Examples of compounds which are suitable components in mixtures for uses in crop protection are:
fungicides:
aldimorph, ampropylfos, ampropylfos-potassium, andoprim, anilazin, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvone, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezin, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazol, imazalii, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidon, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole tecloftalam, tecnazene, tetcyclacis, tetraconazole, thiabendazole, thicyofen, thifluzamide, thiophanate-methyl, thiram, tioxymid, toiclofos-methyl, tolylfluanid, triadimefon, triadimenol, triazbutil, triazoxide, trichiamide, tricyclazole, tridemorph, triflumizole, triforine, triticonazole, uniconazole, validamycin A, vinclozolin, viniconazole, zarilamide, zineb, ziram and also Dagger G,
OK-8705,
OK-8801,
α-(1,1-dimethylethyl)-β-(2-phenoxyethyl)-1H-1,2,4-triazol-1-ethanol,
α-(2,4-dichlorophenyl)-β-fluoro-b-propyl-1H-1,2,4-triazol-1-ethanol,
α-(2,4-dichlorophenyl)-β-methoxy-a-methyl-1H-1,2,4-triazol-1-ethanol,
α-(5-methyl-1,3-dioxan-5-yl)-β-[[4-(trifluoromethyl)-phenyl]-methylene]-1H-1,2,4-triazol-1-ethanol,
(5RS,6RS)-6-hydroxy-2,2,7,7-tetramethyl-5-(1H-1,2,4-triazol-1-yl)-3-octanone,
(E)-a-(methoxyimino)-N-methyl-2-phenoxy-phenylacetamide,
1-isopropyl {2-methyl-1-[[[1-(4-methylphenyl)-ethyl]-amino]-carbonyl]-propyl}-carbamate
1-(2,4-dichlorophenyl)-2-(1H-1,2,4-triazol-1-yl)-ethanone O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy-4'-tri fluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy4-O-(4-O-methyl-β-D-glycopyranosyl)-a-D-glucopyranosyl]-amino]4-methoxy-1H-pyrrolo[2,3-d] pyrimidine-5-carbonitrile,
2-aminobutane,
2-bromo-2-(bromomethyl)-pentanonitrile,
2-chloro-N-(2,3-dihydro-1,1,3-trimethyl-1H-inden4-yl)-3-pyridinecarboxamide,
2-chloro-N-(2,6-dimethylphenyl)-N-(isothiocyanatomethyl)-acetamide,
2-phenylphenol(OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro [4.5]decane-2-methanamine,
8-hydroxyquinoline sulphate,
9H-xanthene-9-carboxylic acid 2-[(phenylamino)-carbonyl]-hydrazide,
bis-(1-methylethyl) 3-methyl4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethylmorpholine hydrochloride,
ethyl [(4-chlorophenyl)-azo]-cyanoacetate,
potassium hydrogen carbonate,
sodium methanetetrathiolate,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro4-hydroxyphenyl)-1-methyl-cyclohexanecarboxamide.
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
sodium N-formyl-N-hydroxy-DL-alaninate,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
insecticides/acaricides/nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cyclopene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusate-sodium, dofenapyn, eflusilanate, emamectin, empenthrin, endosulfan, Entomopfthora spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses halofenozide, HCH, heptenophos, hexaflumuron, hexythiazox, hydroprene, imidacloprid, isazofos, isofenphos, isoxathion, ivermectin, nuclear polyhedrosis viruses lambda-cyhalothrin, lufenuron malathion, mecarbam, metaldehyde, methamidophos, Metharhizium anisopliae, Metharhizium flavoviride, methidathion, methiocarb, methomyl, methoxyfenozide, metolcarb, metoxadiazone, mevinphos, milbemectin, monocrotophos, naled, nitenpyram, nithiazine, novaluron omethoate, oxamyl, oxydemethon M Paecilomyces fumosoroseus, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben,pyridathion, pyrimidifen, pyriproxyfen, quinalphos, ribavirin salithion, sebufos, silafluofen, spinosad, sulfotep, suiprofos, tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, Verticillium lecanii
YI 5302
zeta-cypermethrin, zolaprofos
(1R-cis)-[5-(phenylmethyl)-3-furanyl]-methyl-3-[(dihydro-2-oxo-3(2H)-furanylidene)-methyl]-2,2-dimethylcyclopropanecarboxylate
(3-phenoxyphenyl)-methyl 2,2,3,3-tetramethylcyclopropanecarboxylate
1-[(2-chloro-5-thiazolyl)methyl]tetrahydro-3,5-dimethyl-N-nitro-1,3,5-triazin-2(1H)-imine
2-(2-chloro-6-fluorophenyl)4-[4-(1,1-dimethylethyl) phenyl]-4,5-dihydro-oxazole
2-(acetlyoxy)-3-dodecyl-1,4-naphthalenedione
2-chloro-N-[[[4-(1-phenylethoxy)-phenyl]-amino]-carbonyl]-benzamide
2-chloro-N-[[[4-(2,2-dichloro-1,1-difluoroethoxy)-phenyl]-amino]-carbonyl]-benzamide
3-methylphenyl propylcarbamate
4-[4-(4-ethoxyphenyl)4-methylpentyl]-1-fluoro-2-phenoxybenzene
4-chloro-2-(1,1-dimethylethyl)-5-[[2-(2,6-dimethyl-4-phenoxyphenoxy)ethyl]thio]-3(2H)-pyridazinone
4-chloro-2-(2-chloro-2-methylpropyl )-5-[(6-iodo-3-pyridinyl)methoxy]-3(2H)-pyridazinone
4-chloro-5-[(6-chloro-3-pyridinyl)methoxy]-2-(3,4-dichlorophenyl)-3(2H)-pyridazinone
*Bacillus thuringiensis* strain EG-2348
Benzoic acid [2-benzoyl-1-(1,1-dimethylethyl)-hydrazide
2,2-dimethyl-3-(2,4-dichlorophenyl)-2-oxo-1-oxaspiro[4.5] dec-3-en-4-yl butanoate
[3-[(6-chloro-3-pyridinyl)methyl]-2-thiazolidinylidene]-cyanamide
dihydro-2-(nitromethylene)-2H-1,3-thiazine-3(4H)-carboxaldehyde
ethyl [2-[[1,6-dihydro-6-oxo-1-(phenylmethyl)4-pyridazinyl]oxy]ethyl]-carbamate
N-(3,4,4-trifluoro-1-oxo-3-butenyl)-glycine
N-(4-chlorophenyl)-3-[4-(difluoromethoxy)phenyl]-4,5-dihydro4-phenyl-1H-pyrazole-1-carboxamide
N-[(2-chloro-5-thiazolyl)methyl]-N'-methyl-N"-nitro-guanidine
N-methyl-N'-(1-methyl-2-propenyl)-1,2-hydrazinedicarbothioamide
N-methyl-N'-2-propenyl-1,2-hydrazinedicarbothioamide
O,O-diethyl [2-(dipropylamino)-2-oxoethyl]-ethylphosphoramidothioate A mixture with other known active compounds such as herbicides, or with fertilizers and growth regulators, is also possible.

Examples of components in mixtures which prove particularly advantageous for uses in the protection of materials are the following:

triazoles such as:
azaconazole, azocyclotin, bitertanol, bromuconazole, cyproconazole, diclobutrazole, difenoconazole, diniconazole, epoxyconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazol, penconazole, propioconazole, (±)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, tebuconazole, tetraconazole, triadimefon, triadimenol, triapenthenol, triflumizole, triticonazole, uniconazole and their metal salts and acid adducts;

imidazoles such as:
clotrimazole, bifonazole, climbazole, econazole, fenapamil, imazalil, isoconazole, ketoconazole, lombazole, miconazole, oxpoconazole, pefurazoate, prochloraz, triflumizole, thiazolcar 1-imidazolyl-1-(4'-chlorophenoxy)-3,3-dimethylbutan-2-one and their metal salts and acid adducts;

pyridines and pyrimidines such as:
ancymidol, buthiobate, fenarimol, nuarimol, triamirol;

succinate dehydrogenase inhibitors such as:
benodanil, carboxin, carboxim sulphoxide, cyclafluramid, fenfuram, flutanil, furcarbanil, furmecyclox, mebenil, mepronil, methfuroxam, metsulfovax, pyro-carbolid, oxycarboxin, Shirlan, Seedvax;

naphthalene derivatives such as:
terbinafine, naftifine, butenafine, 3-chloro-7-(2-aza-2,7,7-trimethyl-oct-3-en-5-ine);

sulphenamides such as:
dichlorfluanid, tolylfluanid, folpet, fluorfolpet; captan, captofol;
benzimidazoles such as:
carbendazim, benomyl, fuberidazole, thiabendazole or their salts;
morpholine derivatives such as:
aldimorph, dimethomorph, dodemorph, falimorph, fenpropidin, fenpropimorph, tridemorph, trimorphamid and their arylsulphonates such as, for example, p-toluenesulfonic acid and p-dodecylphenyl-sulphonic acid;
benzothiazoles such as:
2-mercaptobenzothiazole;
benzothiophene dioxides such as:
benzo[b]thiophene S,S-dioxide carboxylic acid cyclohexylamide;
benzamides such as:
2,6-dichloro-N-(4-trifluoromethylbenzyl)-benzamide, tecloftalam;
boron compounds such as:
boric acid, boric esters, borax;
formaldehyde and formaldehyde-releasing compounds such as:
benzyl alcohol mono(poly)hemiformal, n-butanol hemiformal, dazomet, ethylene glycol hemiformal, hexahydro-S-triazine, hexamethylenetetramine, N-hydroxymethyl-N'-methylthiourea, N-methylolchloroacetamide, oxazolidine, paraformaldehyde, taurolin, tetrahydro-1,3-oxazine, N-(2-hydroxypropyl)-amine-methanol;
isothiazolinones such as:
N-methylisothiazolin-3-one, 5-chloro-N-methylisothiazolin-3-one, 4,5-dichloro-N-octylisothiazolin-3-one, 5-chloro-N-octylisothiazolinone, N-octyl-isothiazolin-3-one, 4,5-trimethylene-isothiazolinone, 4,5-benzisothiazolinone, N-n-butylisothiazolinone;
aldehydes such as:
cinnamaldehyde, formaldehyde, glutardialdehyde, β-bromocinnamaldehyde;
thiocyanates such as:
thiocyanatomethylthiobenzothiazole, methylene bisthiocyanate;
quaternary ammonium compounds such as:
benzalkonium chloride, benzyldimethyltetradecylammonium chloride, benzyldimethyldodecylammonium chloride, dichlorobenzyl-dimethyl-alkyl-ammonium chloride, didecyldimethylammonium chloride, dioctyldimethyl-ammonium chloride, N-hexadecyl-trimethylammonium chloride, 1-hexadecyl-pyridinium chloride;
iodine derivatives such as:
diiodomethyl-p-tolylsulphone, 3-iodo-2-propinyl alcohol, 4-chlorophenyl-3-iodopropargylformal, 3-bromo-2,3-diiodo-2-propenyl ethylcarbamate, 2,3,3-triiodo-allyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexylcarbamate, 3-iodo-2-propinyl phenylcarbamate;
phenols such as:
tribromophenol, tetrachlorophenol, 3-methyl4-chlorophenol, 3,5-dimethyl-4-chlorophenol, phenoxyethanol, dichlorophene, 2-benzyl-4-chlorophenol, 5-chloro-2-(2,4-dichlorophenoxy)-phenol, hexachlorophene, p-hydroxybenzoate, o-phenyl-phenol, m-phenylphenol, p-phenylphenol and their alkali metal and alkaline earth metal salts;

microbicides with activated halogen group such as:
bronopol, bronidox, 2-bromo-2-nitro-1,3-propanediol, 2-bromo-4'-hydroxy-aceto-phenone, 1-bromo-3-chloro-4,4,5,5-tetramethyl-2-imidazoldinone, β-bromo-β-nitrostyrene, chloroacetamide, chloroamine T, 1,3-dibromo-4,4,5,5-tetrametyl-2-imidazoldinone, dichloramine T, 3,4-dichloro-(3H)-1,2-dithiol-3-one, 2,2-dibromo-3-nitrilepropionamide, 1,2-dibromo-2,4-dicyanobutane, halane, halazone, mucochloric acid, phenyl-(2-chloro-cyanovinyl) sulphone, phenyl-(1,2-dichloro-2-cyanovinyl) sulphone, trichioroisocyanuric acid;
pyridines such as:
1-hydroxy-2-pyridinethione (and their Na, Fe, Mn, Zn salts), tetrachloro-4-methylsulphonylpyridine, pyrimethanol, mepanipyrim, dipyrithione, 1-hydroxy-4-methyl-6-(2,4,4-trimethylpentyl)-2(1H)-pyridine;
methoxyacrylates or the like such as:
methyl (E)-methoximino[alpha-(o-tolyloxy)-o-tolyl]acetate,
(E)-2-methoxyimino-N-methyl-2-(2-phenoxyphenyl)acetamide,
(E)-2-{2-[6-(2-cyanophenoxy)pyrimidin-4-yloxy]phenyl}3-methoxyacrylate,
O-methyl-2-[([3-methoximino-2-butyl)imino]oxy)o-tolyl]-2-methoximinoacetimidate,
2-[[[[1-(2,5-dimethylphenyl)ethylidene]amino]oxy]methyl]-.alpha.-(methoximino)-N-metyl-benzeneacetamide,
alpha-(methoxyimino)-N-methyl-2-[[[[1-[3-(trifluoromethyl)phenyl]-ethylidene]amino]oxy]methyl]-benzeneacetamide,
methyl alpha-(methoxyimino)-2-[[[[1-[3-(trifluoromethyl)phenyl]-ethylidene]amino]oxy]methyl]-benzeneacetate,
methyl alpha-(methoxymethylene)-2-[[[[1-[3-(trifluoromethyl)phenyl]-ethylidene]amino]oxy]methyl]-benzeneacetate,
2-[[[5-chloro-3-(trifluoromethyl)-2-pyridinyl]oxy]methyl]-.alpha.-(methoxyimino)-N-methyl-benzeneacetamide,
methyl 2-[[[cyclopropyl [(4-ethoxyphenyl)imino]methyl]thio]methyl]-.alpha.-(methoxyimino)-benzeneacetate,
alpha-(methoxyimino)-N-methyl-2-(4-methyl-5-phenyl-2,7-dioxa-3,6-diazaocta-3,5-dien-1-yl)-benzeneacetamide,
methyl alpha-(methoxymethylene)-2-(4-methyl-5-phenyl-2,7-dioxa-3,6-diazaocta-3,5-dien-1-yl)-benzeneacetate,
alpha-(methoxyimino)-N-methyl-2-[[[1-[3-(trifluoromethyl)phenyl]-ethoxy]imino]methyl]-benzeneacetamide,
2-[[(3,5-dichloro-2-pyridinyl)oxy]methyl]-.alpha.-(methoxyimino)-N-methyl-benzeneacetamide,
methyl 2-[4,5-dimethyl-9-(4-morpholinyl)-2,7-dioxa-3,6-diazanona-3,5-dien-1-yl]-.alpha.-(methoxymethylene)-benzeneacetate;
metal soaps such as:
tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate and zinc benzoate;
metal salts such as:
copper hydroxycarbonate, sodium dichromate, potassium dichromate, potassium chromate, copper sulphate, copper chloride, copper borate, zinc fluorosilicate, copper fluorosilicate;
oxides such as:
tributyltin oxide, $Cu_2O$, CuO, ZnO;
dithiocarbamates such as:
cufraneb, ferban, potassium N-hydroxymethyl-N'-methyldithiobarbamate, Na or K dimethyldithiocarbamate, macozeb, maneb, metam, metiram, thiram, zineb, ziram;

nitriles such as:
2,4,5,6-tetrachloroisophthalodinitrile, disodium cyanodithioimidocarbamate;
quinolines such as:
8-hydroxyquinoline and their Cu salts;
other fungicides and bactericides such as:
5-hydroxy-2(5H)-furanone; 4,5-benzodithiazolinone, 4,5-trimethylenedithiazolinone, N-(2-p-chlorobenzoylethyl)-hexaminium chloride, 2-oxo-2-(4-hydroxy-phenyl)-acethydroximoyl chloride, tris-N-(cyclohexyldiazeniumdioxy)-aluminium, N-(cyclohexyldiazeniumdioxy)-tributyltin or K salts, bis-N-(cyclohexyldiazeniumdioxy)-copper;
Ag, Zn or Cu-containing zeolites, alone or embedded in polymeric materials.

Very especially preferred are mixtures for the protection of materials containing azaconazole, bromuconazole, cyproconazole, dichlobutrazol, diniconazole, hexaconazole, metaconazole, penconazole, propiconazole, tebuconazole, dichlofluanid, tolylfluanid, fluorfolpet, methfuroxam, carboxin, benzo[b]thiophene S,S-dioxide carboxylic acid cyclohexylamide, fenpiclonil, 4-(2,2-difluoro-1,3-benzodioxol4-yl)-1H-pyrrole-3-carbonitrile, butenafine, imazalil, N-methyl-isothiazolin-3-one, 5-chloro-N-methylisothiazolin-3-one, N-octylisothiazolin-3-one, dichloro-N-octylisozhiazolinone, mercaptobenthiazole, thiocyanatomethylthiobenzothiazole, benzisothiazolinone, N-n-butylisothiazolinone, N-(2-hydroxypropyl)-aminomethanol, benzyl alcohol (hemi)formal, N-methylolchloroacetamide, N-(2-hydroxypropyl)-amine-methanol, glutaraldehyde, omadine, di methyl dicarbon ate, and/or 3-iodo-2-propinyl n-butylcarbamate.

In addition to the abovementioned fungicides and bactericides for use in the protection of materials, highly effective mixtures are also prepared with other active compounds:
insecticides/acaricides/nematicides:
abamectin, acephate, acetamiprid, acrinathrin, alanycarb, aldicarb, aldoxycarb, aldrin, allethrin, alpha-cypermethrin, amitraz, avermectin, AZ 60541, azadirachtin, azinphos A, azinphos M, azocyclotin, *Bacillus thuringiensis,* barthrin, 4-bromo-2(4-chlorophenyl)-1-(ethoxymethyl)-5-(trifluoromethyl)-1H-pyrrole-3-carbonitrile, bendiocarb, benfuracarb, bensultap, beta-cyfluthrin, bifenthrin, bioresmethrin, bioallethrin, bromophos A, bromophos M, bufencarb, buprofezin, butathiophos, butocarboxin, butoxycarboxim, cadusafos, carbaryl, carbofuran, carbophenothion, carbosulfan, cartap, quino-methionate, cloethocarb, chlordane, chlorethoxyfos, chlorfenvinphos, chlorfluazuron, chlormephos, N-[(6-chloro-3-pyridinyl )-methyl ]-N'-cyano-N-methyl-ethanimidamide, chlorpicrin, chlorpyrifos A, chlorpyrifos M, cis-resmethrin, clocythrin, cypophenothrin, clofentezin, coumaphos, cyanophos, cycloprothrin, cyfluthrin, cyhalothrin, cyhexatin, cypermethrin, cyromazin, decamethrin, deltamethrin, demeton M, demeton S, demeton-S-methyl, diafenthiuron, dialiphos, diazinon, 1,2-dibenzoyl-1(1,1-dimethyl)-hydrazine, DNOC, dichlofenthion, dichlorvos, dicliphos, dicrotophos, diflubenzuron, dimethoate, dimethyl-(phenyl)-silyl-methyl-3-phenoxybenzyl ether, dimethyl-(4-ethoxyphenyl)-silylmethyl-3-phenoxybenzyl ether, dimethylvinphos, dioxathion, disulfoton, eflusilanate, emamectin, empenthrin, endosulfan, EPN, esfenvalerate, ethiofencarb, ethion, ethofenprox, etrimphos, fenamiphos, fenazaquin, fenbutatin oxide, fenfluthrin, fenitrothion, fenobucarb, fenothiocarb, fenoxycarb, fenpropathrin, fenpyrad, fenpyroximate, fensulfothion, fenthion, fenvalerate, fipronil, fluazuron, flucycloxuron, flucythrinate, flufenoxuron, flumethrin, flufenprox, fluvalinate, fonophos, formethanate, formothion, fosmethilan, fosthiazate, fubfenprox, furathiocarb, HCH, heptenophos, hexaflumuron, hexythiazox, hydramethylnon, hydroprene, imidacloprid, iodfenfos, iprobenfos, isazophos, isoamidophos, isofenphos, isoprocarb, isoprothiolane, isoxathion, ivermectin, lama-cyhalothrin, lufenuron, kadedrin lambda-cyhalothrin, lufenuron, malathion, mecarbam, mervinphos, mesulfenphos, metaldehyde, methacrifos, methamidophos, methidathion, methiocarb, methomyl, metalcarb, milbemectin, monocrotophos, moxiectin, naled, NC 184, NI 125, nicotine, nitenpyram, omethoate, oxamyl, oxydemethon M, oxydeprofos, parathion A, parathion M, penfluron, permethrin, 2-(4-phenoxyphenoxy)-ethyl ethylcarbamate, phenthoate, phorate, phosalone, phosmet, phosphamidon, phoxim, pirimicarb, pirimiphos M, pirimiphos A, prallethrin, profenophos, promecarb, propaphos, propoxur, prothiophos, prothoate, pymetrozin, pyrachlophos, pyridaphenthion, pyresmethrin, pyrethrum, pyridaben, pyrimidifen, pyriproxifen, quinalphos, resmethrin, RH-7988, rotenone, salithion, sebufos, silafluofen, sulfotep, sulprofos, tau-fluvalinate, tar oils, tebufenozide, tebufenpyrad, tebupirimphos, teflubenzuron, tefluthrin, temephos, terbam, terbufos, tetrachlorvinphos, tetramethrin, tetramethacarb, thiacloprid, thiafenox, thiamethoxam, thiapronil, thiodicarb, thiofanox, thiazophos, thiocyclam, thiomethon, thionazin, thuringiensin, tralomethrin, triarathen, triazophos, triazamate, triazuron, trichlorfon, triflumuron, trimethacarb, vamidothion, XMC, xylylcarb, zetamethrin;
molluscicides
fentin acetate, metaldehyde, methiocarb. niclosamide;
herbicides and algicides
acetochlor, acifluorfen, aclonifen, acrolein, alachlor, alloxydim, ametryn, amidosulfuron, amitrole, ammonium sulphamate, anilofos, asulam, atrazine, aziptrotryne, azimsulfuron, benazolin, benfluralin, benfuresate, bensulfuron, bensulfide, bentazone, benzofencap, benzthiazuron, bifenox, borax, bromacil, bromobutide, bromofenoxim, bromoxynil, butachlor, butamifos, butralin, butylate, bialaphos, benzoyl-prop, bromobutide, carbetamide, chlomethoxyfen, chloramben, chlorbromuron, chlorflurenol, chloridazon, chlorimuron, chlomitrofen, chloroacetic acid, chlorotoluron, chloroxuron, chlorpropham, chlorsulfuron, chlorthal, chlorthiamid, cinmethylin, cinofulsuron, clethodim, clomazone, chlomeprop, clopyralid, cyanamide, cyanazine, cycloate, cycloxydim, chloroxynil, clodinafop-propargyl, cumyluron, CGA 248757, clometoxyfen, cyhalofop, clopyrasuluron, cyclosulfamuron, dichlorprop, dichlorprop-P, diclofop, diethatyl, difenoxuron, difenzoquat, diflufenican, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D, daimuron, dalapon, dazomet, 2,4-DB, desmedipham, desmetryn, dicamba, dichlobenil, dimethamid, dithiopyr, dimethametryn, eglinazine, endothal, EPTC, esprocarb, ethalfluralin, ethidimuron, ethofumesate, ethobenzanid, ethoxyfen, ET 751, ethametsulfuron, fenoxaprop, fenoxaprop-P, fenuron, flamprop, flamprop-M, flazasulfuron, fluazifop, fluazifop-P, fuenachlor, fluchloralin, flumeturon, fluorocglycofen, fluoronitrofen, flupropanate, flurenol, fluridone, flurochloridone, fluroxypyr, fomesafen, fosamine, flamprop-isopropyl, flamprop-isopropyl-L, flumiclorac-pentyl, flumipropyn, flumioxzim, flurtatone, flumioxzim, glyphosate, glufosinate-ammonium haloxyfop, hexazinone, imazamethabenz, isoproturon, isoxaben, isoxapyrifop, imazapyr, imazaquin, imazethapyr, ioxynil, isopropalin, imazosulfuron,

KUH 911, KUH 920 lactofen, lenacil, linuron, LS830556,

MCPA, MCPA-thioethyl, MCPB, mecoprop, mecoprop-P, mefenacet, mefluidide, metam, metamitron, metazachlor, methabenzthiazuron, methazole, methoroptryne, methyldymron, methyl isothiocyanate, metobromuron, metoxuron, metribuzin, metsulfuron, molinate, monalide, monolinuron, MSMA, metolachlor, metosulam, metobenzuron, naproanilide, napropamide, naptalam, neburon, nicosulfuron, norflurazon, sodium chlorate, oxadiazon, oxyfluorfen, orbencarb, oryzalin, quinchlorac, quinmerac, propyzamide, prosulfocarb, pyrazolate, pyrazolsulfuron, pyrazoxyfen, pyributicarb, pyridate, paraquat, pebulate, pendimethalin, pentachlorophenol, pentanochlor, petroleum oils, phenmedipham, picloram, piperophos, pretilachlor, primisulfuron, prodiamine, prometryn, propachlor, propanil, propaquizafob, propazine, propham, pyrithiobac, quinmerac, quinocloamine, quizalofop, quizalofop-P, rimsulfuron sethoxydim, sifuron, simazine, simetryn, sulfometuron, sulfentrazone, sulcotrione, sulfosate, tar oils, TCA, tebutam, tebuthiuron, terbacil, terbumeton, terbuthylazine, terbutryn, thiazafluoron, thifensulfuron, thiobencarb, thiocarbazil, tralkoxydim, triallate, triasulfuron, tribenuron, triclopyr, tridiphane, trietazine, trifluralin, tycor, thdiazimin, thiazopyr, triflusulfuron, vernolate.

The active compounds can be applied as such, in the form of their formulations or the use forms prepared therefrom, such as ready-to-use solutions, suspensions, wettable powders, pastes, soluble powders, dusts and granules. They are used in the customary manner, for example by pouring, spraying, atomizing, scattering, dusting, foaming, brushing on and the like. It is furthermore possible to apply the active compounds by the ultra-low-volume method or to inject the active compound formulation or the active compound itself into the soil. The seeds of the plants may also be treated.

When using the active compounds according to the invention as fungicides, the application rates can be varied within a substantial range, depending on the type of application. For the treatment of plant parts, the application rates of active compound are generally between 0.1 and 10 000 g/ha, preferably between 10 and 1000 g/ha. For the treatment of seed, the application rates of active compound are generally between 0.001 and 50 g per kilogram of seed, preferably between 0.01 and 10 g per kilogram of seed. For the treatment of the soil, the application rates of active compound are generally between 0.1 and 10 000 g/ha, preferably between 1 and 5000 g/ha.

The compositions used for the protection of industrial materials comprise the active compounds in general in an amount of from 1 to 95%, preferably from 10 to 75%.

The use concentrations of the active compounds according to the invention depend on the type and the occurrence of the microorganisms to be controlled and on the composition of the material to be protected. The optimal use concentration can be determined by test series. In general, the use concentrations are in the range of from 0.001 to 5% by weight, preferably from 0.05 to 1.0% by weight, based on the material to be protected.

The active compounds are well tolerated by plants, show advantageous toxicity to warm-blooded species and are thus suitable for controlling animal pests, in particular insects, arachnids and nematodes, which are found in agriculture, in forests, in the protection of stored products and of materials, and in the hygiene sector. They can preferably be used as crop protection agents. They are active against normally sensitive and resistant species and against all or individual developmental stages. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus,* Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus,* Gryllotalpa spp., *Locusta migratoria migratorioides,* Melanoplus spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, Reticulitermes spp.

From the order of the Phthiraptera, for example, *Pediculus humanus corporis,* Haematopinus spp., Linognathus spp., Trichodectes spp., Damalinia spp.

From the order of the Thysanoptera, for example, *Hercinothrips femoralis, Thrips tabaci, Thrips palmi, Frankliniella accidentalis.*

From the order of the Heteroptera, for example, Eurygaster spp., *Dysdercus intermedius, Piesma quadrata, Cimex lectularius, Rhodnius prolixus,* Triatoma spp.

From the order of the Homoptera, for example, *Aleurodes brassicae, Bemisia tabaci, Trialeurodes vaporariorum, Aphis gossypli, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantil, Aspidiotus hederae,* Pseudococcus spp., Psylla spp.

From the order of the Lepidoptera, for example, *Pectinophora gossypiella, Bupalus piniarius, Cheimatobia brumata, Lithocolletis blancardella, Hyponomeuta padelia, Plutella xylostella, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Mamestra brassicae, Panolis flammea,* Spodoptera spp., Trichoplusia ni, *Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana,* Cnaphalocerus spp.

From the order of the Coleoptera, for example, *Anobium punctatum, Rhizopertha dominica, Bruchidius obtectus,*

Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon soistitialis, Costelytra zealandica.

From the order of the Hymenoptera, for example, Diprion spp., Hoplocampa spp., Lasius spp., Monomorium pharaonis, Vespa spp.

From the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae, Tipula paludosa, Hylemyia spp., Liriomyza spp.

From the order of the Siphonaptera, for example, Xenopsylla cheopis, Ceratophyllus spp.

From the class of the Arachnida, for example, Scorpio maurus, Latrodectus mactans, Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Hemitarsonemus spp., Brevipalpus spp.

The plant-parasitic nematodes include, for example, Pratylenchus spp., Radopholus similis, Ditylenchus dipsaci, Tylenchulus semipenetrans, Heterodera spp., Globodera spp., Meloidogyne spp., Aphelenchoides spp., Longidorus spp., Xiphinema spp., Trichodorus spp., Bursaphelenchus spp.

The compounds of the formula (I) according to the invention can be employed particularly successfully for controlling plant-injurious insects such as, for example, against the caterpillars of the diamond-back moth (Plutella maculipennis) or of the green peach aphid (Mycus persicae), and also against plant-injurious mites, such as, for example, against the greenhouse red spider mite (Tetranychus urticae).

Furthermore, when used as insecticides, the active compounds according to the invention in their commercially available preparations and in the use forms prepared with these formulations, may be present as a mixture with synergists. Synergists are compounds by which the action of the active compounds is increased without it being necessary for the synergist added to be active itself.

The active compound content of the use forms prepared from the commercially available formulations can vary within wide limits. The active compound concentration of the use forms can be from 0.0000001 up to 95% by weight of active compound, preferably between 0.0001 and 1% by weight.

They are used in the customary manner adapted to suit the use forms.

When used against hygiene pests and stored-product pests, the active compound is distinguished by an outstanding residual action on wood and clay and by good stability to alkali on limed substrates.

The preparation and the use of the active compounds according to the invention can be seen from the examples which follow.

PREPARATION EXAMPLES

EXAMPLE 1

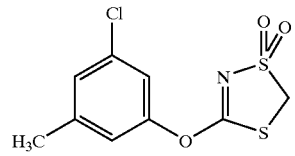

A solution of 0.89 g (6.3 mmol) 3-chloro-5-methylphenol in 0.63 g (6.3 mmol) of triethylamine is added dropwise at room temperature to a solution of 1.0 g (5.8 mmol) of chlorodithiazole dioxide in 5 ml of dimethylformamide. The mixture is stirred for 2 hours at room temperature and then poured into 50 ml of ice-water, and the product which has precipitated is filtered off with suction and dried in vacuo. This gives 1.47 g (91% of theory) of 3-(3-chloro-5-methylphenoxy)-1$\lambda^6$, 4,2-dithiazole-1,1(5H)-dione of melting point 151.2° C.

EXAMPLE 2

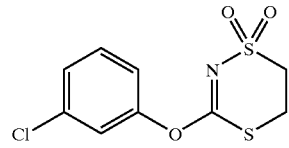

1.0 g (6.5 mmol) of chlorodithiazine dioxide (6-membered ring) are dissolved in 25 ml of dimethylformamide, and a solution of 0.84 g (6.5 mmol) of 3-chlorophenol and 0.66 g (6.5 mmol) of triethylamine in 15 ml of dimethylformamide is added in the course of 5 minutes. The mixture is stirred for 4 hours at room temperature and poured into water, and the precipitate is filtered off with suction, washed with a little ether and dried in vacuo. This gives 0.39 g (22% of theory) of 3-(3-chlorophenoxy)-5,6-dihydro-1H-1$\lambda^6$,4,2-dithiazine-1,1-dione of melting point 170.2° C.

The compounds of the formula (I) stated in Tables 1 and 2 were also obtained analogously to Examples 1 and 2 and to the general description of preparation process a) according to the invention.

TABLE 1

(I-a)

| Ex. | R¹ | R² | R³ | R⁴ | R⁵ | Y | logP | m.p. (° C.) |
|---|---|---|---|---|---|---|---|---|
| 3 | —H | —H | —H | —CF₃ | —H | $\underset{*}{\overset{CH_3}{\diagup}}$ | 2.89 | |
| 4 | *—C(=NOCH₃)—[2-methoxy-5,6-dihydro-1,3-oxazine] | —H | —H | —H | —H | —CH₂— | 1.77 | 162–166 |
| 5 | *—C(=CHOCH₃)—C(=O)OCH₃ | —H | —H | —H | —H | —CH₂— | 2.03 | 124–128 |
| 6 | *—CH₂—[2-yl-5,6-dihydro-1,3-oxazine] | —H | —H | —H | —H | —CH₂— | 1.69 | 156–159 |
| 7 | *—C(=N—O—CH₂CN)—C(=O)OCH₃ | —H | —H | —H | —H | —CH₂— | 1.7 | 109 decomp |

TABLE 1-continued (I-a)

| Ex. | R¹ | R² | R³ | R⁴ | R⁵ | Y | logP | m.p. (° C.) |
|---|---|---|---|---|---|---|---|---|
| 8 | —CH₂—CN | H | H | H | H | —CH₂— | 1.68 | 149–153 |
| 9 | (benzyl amide oxime methyl ether) | H | H | H | H | —CH₂— | 2.13 | 112–114 decomp |
| 10 | (benzyloxy amide oxime methyl ether) | H | H | H | H | —CH₂— | 2.18 | 166 decomp |
| 11 | (amide oxime methyl ether) | H | H | H | H | —CH₂— | 1.33 | 174–176 decomp |

TABLE 1-continued
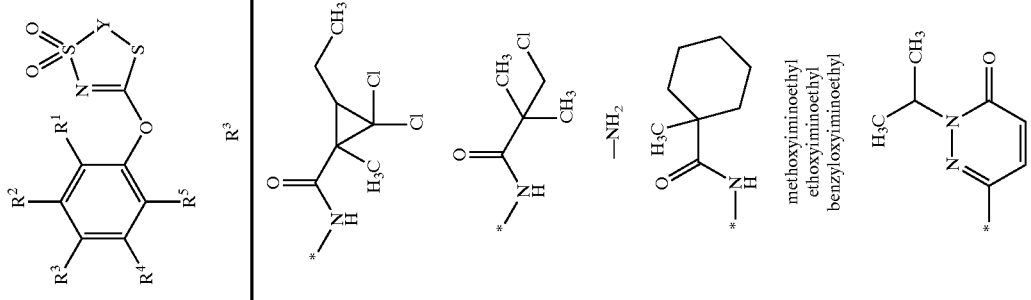
(I-a)
| Ex. | R¹ | R² | R³ | R⁴ | R⁵ | Y | logP | m.p. (° C.) |
|---|---|---|---|---|---|---|---|---|
| 12 | —Cl | —Cl | ![structure: cyclopropane amide with CH₃, CH₃, Cl groups] | —H | —H | —CH₂— | 3.63 | |
| 13 | —Cl | —Cl | ![structure: amide with CH₃, CH₃, Cl groups] | —H | —H | —CH₂— | 2.98 | |
| 14 | —Cl | —Cl | —NH₂ | —H | —H | —CH₂— | | |
| 15 | —H | —H | | —Cl | —Cl | —CH₂— | | |
| 16 | —CH₃ | —H | methoxyiminoethyl | —H | —H | —CH₂— | 2.88 | |
| 17 | —CH₃ | —H | ethoxyiminoethyl | —H | —H | —CH₂— | 3.32 | |
| 18 | —CH₃ | —H | benzyloxyiminoethyl | —H | —H | —CH₂— | 3.92 | |
| 19 | —H | —H | ![pyridazinone structure] | —H | —H | —CH₂— | 2.15 | |
| 20 | —H | —H | methoxyiminoethyl | —H | —H | —CH₂— | 2.62 | |
| 21 | —H | —H | —COCH₃ | —H | —H | —CH₂— | 1.69 | |

TABLE 1-continued (I-a)

| Ex. | R¹ | R² | R³ | R⁴ | R⁵ | Y | logP | m.p. (° C.) |
|---|---|---|---|---|---|---|---|---|
| 22 | —H | —H | benzyloxyiminoethyl | —H | —H | —CH₂— | 3.67 | |
| 23 | —H | —H | allyloxyiminoethyl | —H | —H | —CH₂— | 3.15 | |
| 24 | —H | —H | t-butyloxyiminoethyl | —H | —H | —CH₂— | 3.98 | |
| 25 | —H | benzyloxyiminoethyl | —H | —H | —H | —CH₂— | 3.67 | |
| 26 | —H | methoxyiminoethyl | —H | —H | —H | —CH₂— | 2.65 | |
| 27 | —H | benzoyl | —H | —H | —H | —CH₂— | 2.66 | |
| 28 | —H | t-butyloxyiminoethyl | —H | —H | —H | —CH₂— | 3.94 | |
| 29 | —H | methoxyiminoethyl | —H | NO₂ | —H | —CH₂— | 2.86 | |
| 30 | methoxyiminoethyl | —H | —H | —H | —H | —CH₂— | 2.43 | |
| 31 | —H | methoxyiminoethyl | —H | —O—CH₃ | —H | —CH₂— | 2.51 | |
| 32 | —H | —COOCH₃ | —COOCH₃ | —H | —H | —CH₂— | 1.93 | |
| 33 | —H | [structure] | methoxyiminoethyl | | | —CH₂— | 2.6 | |
| 34 | —H | t-butyl | —OH | —H | —H | —CH₂— | 2.66 | |
| 35 | —H | —H | [oxadiazole structure] | —H | —H | —CH₂— | 1.36 | |
| 36 | —H | —CH=N—NH—COOC₂H₅ | —H | —H | —H | —CH₂— | 1.79 | |
| 37 | —H | —CH₂—N=N—COOC₂H₅ | —H | —H | —O—CH₃ | —CH₂— | 1.86 | |
| 38 | —H | —CH=C(CN)₂ | —H | —H | —H | —CH₂— | 1.59 | |
| 39 | —O—CH₃ | —COCH₃ | —H | —H | —O—CH₃ | —CH₂— | 1.9 | |
| 40 | —H | —COCH₃ | —H | —H | —H | —CH₂— | 1.73 | |

TABLE 1-continued (I-a)

| Ex. | R¹ | R² | R³ | R⁴ | R⁵ | Y | logP | m.p. (° C.) |
|---|---|---|---|---|---|---|---|---|
| 41 | —H | Ph-C(*)=N-O-CH₃ | —H | —H | —H | —CH₂— | 3.28 | |
| 42 | —H | Ph-C(*)=N-O-CH₂-CH=CH₂ | —H | —H | —H | —CH₂— | 3.72 | |
| 43 | —H | Ph-C(*)=N-O-C(CH₃)₃ | —H | —H | —H | —CH₂— | 4.4 | |
| 44 | —H | Ph-C(*)=N-O-CH₂-Ph | —H | —H | —H | —CH₂— | 4.15 | |

TABLE 1-continued
(I-a)
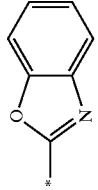
| Ex. | R¹ | R² | R³ | R⁴ | R⁵ | Y | logP | m.p. (° C.) |
|---|---|---|---|---|---|---|---|---|
| 45 | —H | —H | 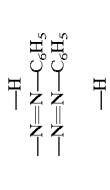 | —H | —H | —CH₂— | 2.88 | |
| 46 | —H | —CH₂OH | —N=N—C₆H₅ | —H | —H | —CH₂— | 1.23 | |
| 47 | —H | —H | —N=N—C₆H₅ | —H | —H | —CH₂— | 3.47 | |
| 48 | —Cl | —H | —N=N—C₆H₅ | —H | —H | —CH₂— | 3.96 | |
| 49 | —H |  | —H | —H | —H | —CH₂— | 2.43 | |
| 50 | —H | —H |  | —H | —H | —CH₂— | 3.3 | |
| 51 |  | —H | —N=N—C₆H₅ | —H | —H | —CH₂— | 3.06 | |

TABLE 1-continued (I-a)

| Ex. | R$^1$ | R$^2$ | R$^3$ | R$^4$ | R$^5$ | Y | logP | m.p. (° C.) |
|---|---|---|---|---|---|---|---|---|
| 52 | —H | —CH$_3$ | —S—CF$_3$ | —H | —H | —CH$_2$— | 3.39 | |
| 53 | —H | —H | —CH=N—CH$_3$ | —H | —H | —CH$_2$— | 2.33 | |
| 54 | —H | —CH$_3$ | —S—CH$_3$ | —H | —H | —CH$_2$— | 2.75 | |
| 55 | —H | —CH$_3$ | —CO—CH$_2$—SCN | —H | —H | —CH$_2$— | 2.01 | |
| 56 | —H | (O—C=N—O ring) | —H | —H | —H | —CH$_2$— | 1.86 | |
| 57 | —COC$_2$H$_5$ | —H | —H | —H | —H | —CH$_2$— | 2.04 | |
| 58 | —H | —O—CH$_3$ | —COCH$_3$ | —H | —H | —CH$_2$— | 1.88 | |
| 59 | —H | —H | —SO$_2$C$_2$H$_5$ | —H | —H | —CH$_2$— | 1.54 | |
| 60 | —H | —CH$_3$ | —SCN | —CH$_3$ | —H | —CH$_2$— | 2.55 | |
| 61 | —H | —H | —CH=N—N(CH$_3$)$_2$ | —H | —H | —CH$_2$— | 2.16 | |
| 62 | —H | —H | (4,5-dimethylthiazol-2-ylthio) | —H | —H | —CH$_2$— | 2.91 | |
| 63 | —H | —H | (4,5-dimethylpyrimidin-2-ylthio) | —H | —H | —CH$_2$— | 2.55 | |
| 64 | —NH—CH$_3$ | —H | —CO—N(C$_2$H$_5$)$_2$ | —H | —H | —CH$_2$— | 2 | |
| 65 | —H | —H | —CO-benzyl | —H | —H | —CH$_2$— | 2.76 | |
| 66 | —H | —H | 4-methoxybenzoyl | —H | —H | —CH$_2$— | 2.67 | |

TABLE 1-continued
(I-a)
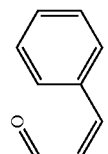
| Ex. | R¹ | R² | R³ | R⁴ | R⁵ | Y | logP | m.p. (° C.) |
|---|---|---|---|---|---|---|---|---|
| 67 | —H | —H | 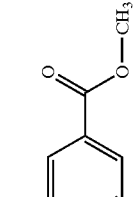 | —H | —H | —CH₂— | 3.06 | |
| 68 | —H | —H |  | —H | —H | —CH₂— | 1.59 | |
| 69 | —H | 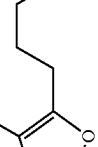 | —H | —H | —H | —CH₂— | 3.43 | |
| 70 | —H | —H | 4-phenylbenzoyl | —H | —H | —CH₂— | 3.72 | |
| 71 | —H | —H | (structure shown above) | —H | —H | —CH₂— | 4.28 | |

TABLE 1-continued (I-a)

| Ex. | R¹ | R² | R³ | R⁴ | R⁵ | Y | logP | m.p. (° C.) |
|---|---|---|---|---|---|---|---|---|
| 72 | —H | —H | —O—C(O)—NH—N=C(CH₃)* (ethoxycarbonylhydrazono-ethyl) | —H | —H | —CH₂— | 1.86 | |
| 73 | —H | —H | 2-phenyl-2,3-dihydro-1-benzothiepin-5-yl* | —H | —H | —CH₂— | 4.19 | |
| 74 | —COCH₃ | —COCH₃ | —H | —NO₂ | —H | —CH₂— | 1.95 | |
| 75 | —H | —H | —H | —O—CH₃ | —H | —CH₂— | 1.83 | |
| 76 | —H | 4-(methoxycarbonyl)phenyl-N=* | —H | —H | —H | —CH₂— | 1.61 | |
| 77 | —O—CH₃ | methoxyiminoethyl | —H | —H | —O—CH₃ | —CH₂— | 2.58 | |
| 78 | —H | 5-methoxy-1,1-dioxo-1,3-dithiolan-2-ylidene* | —H | —COCH₃ | —H | —CH₂— | 1.8 | |

TABLE 1-continued (I-a)

| Ex. | R¹ | R² | R³ | R⁴ | R⁵ | Y | logP | m.p. (° C.) |
|---|---|---|---|---|---|---|---|---|
| 79 | —O—CH₃ | —H | (N-allyl phthalimide group) | —H | —H | —CH₂— | 2.63 | |
| 80 | —H | H₃C-CH(OH)- | —H | —H | —H | —CH₂— | 1.48 | |
| 81 | —H | 2,4-dinitrostyryl | —H | —H | —H | —CH₂— | 3.22 | |
| 82 | —H | CH₃-CH(OH)-(CH₂)₃- | —H | —H | —H | —CH₂— | 2.87 | |
| 83 | —H | —H | 4-chlorophenylsulphonyl | —H | —H | —CH₂— | 2.72 | |
| 84 | —H | —CH₃ | 2-methyl-4-nitrophenylthio | —H | —H | —CH₂— | 3.94 | |
| 85 | —NO₂ | —H | —H | —H | —H | —CH₂— | 3.28 | |
| 86 | —H | 4-nitrostyryl | 4-chlorobenzoyl | —H | —H | —CH₂— | 3.17 | |

TABLE 1-continued (I-a)

| Ex. | R¹ | R² | R³ | R⁴ | R⁵ | Y | logP | m.p. (° C.) |
|---|---|---|---|---|---|---|---|---|
| 87 | H | —CH=CH—Ph (styryl) | H | —O—CH₃ | H | —CH₂— | 3.62 | |
| 88 | H | H | thiazoline-O—CH₂—* | H | H | —CH₂— | 1.88 | |
| 89 | H | —C(CH₃)=CH—NO₂ | H | H | H | —CH₂— | 2.46 | |
| 90 | H | —O—CH₂CH₂—O—CH₂CH₂—OH | H | H | H | —CH₂— | 1.39 | |
| 91 | H | H | H | H | H | —CH₂— | 1.37 | 185.8 |
| 92 | H | Cl | H | H | H | —CH₂— | | 128.6 |
| 93 | H | H | Cl | H | H | —CH₂— | | 138.5 |
| 94 | H | H | H | H | Cl | —CH₂— | | 177.5 |
| 95 | Cl | H | Cl | H | H | —CH₂— | | 160.7 |
| 96 | —COCH₃ | H | Cl | H | Cl | —CH₂— | | 117.1 |
| 97 | H | H | Cl | H | Cl | —CH₂— | | 105 |
| 98 | benzyl | H | t-butyl | H | H | —CH₂— | | 160.4 |
| 99 | H | Cl | Cl | H | H | —CH₂— | | 156.9 |
| 100 | Cl | H | Cl | Cl | H | —CH₂— | | 215.5 |
| 101 | Cl | H | Cl | H | H | —CH₂— | | 140.9 |
| 102 | H | H | H | Cl | H | —CH₂— | | 84.4 |
| 103 | H | H | —O—CH₃ | H | H | —CH₂— | | 127.2 |
| 104 | H | H | CH₃ | H | H | —CH₂— | | 113.1 |
| 105 | H | CH₃ | —NO₂ | H | H | —CH₂— | | 204.30 |
| 106 | H | H | H | H | H | —CH₂— | | |
| 107 | —Br | H | H | H | H | —CH₂— | 2.3 | |
| 108 | H | —CN | H | H | H | —CH₂— | 1.69 | |
| 109 | —F | H | H | H | H | —CH₂— | 2.02 | |
| 110 | —F | H | H | H | H | —CH₂— | 2.05 | |
| 111 | H | —F | H | H | H | —CH₂— | | |

TABLE 1-continued (I-a)

| Ex. | R¹ | R² | R³ | R⁴ | R⁵ | Y | logP | m.p. (° C.) |
|---|---|---|---|---|---|---|---|---|
| 112 | —H | —H | —F | —H | —H | —CH$_2$— | 2.04 | |
| 113 | —H | —CF$_3$ | —H | —H | —H | —CH$_2$— | 2.62 | |
| 114 | —H | t-butyl | —H | —H | —H | —CH$_2$— | 3.27 | |
| 115 | —Cl | —O—CH$_3$ | —H | —CH$_3$— | —H | —CH$_2$— | 2.62 | |
| 116 | —H | —O—CH$_3$ | —H | —Cl | —H | —CH$_2$— | 2.61 | |
| 117 | —O—CH$_3$ | —O—CH$_3$ | —H | —H | —H | —CH$_2$— | 1.82 | |
| 118 | —H | —Br | —O—CH$_3$ | —H | —H | —CH$_2$— | 2.12 | |
| 119 | —CH$_3$ | —H | —H | —H | —H | —CH$_2$— | 2.47 | |
| 120 | —H | —H | phenylsulphonyl | —H | —Cl | —CH$_2$— | 2.83 | |
| 121 | —CH$_3$ | —H | 4-nitrophenylthio | —H | —H | —CH$_2$— | 3.28 | |
| 122 | —H | —H | —Br | —H | —H | —CH$_2$— | 2.52 | |
| 123 | —CH$_3$ | —H | —H | —H | —CH$_3$ | —CH$_2$— | 2.57 | |
| 124 | —CH$_3$ | —H | —OCF$_3$ | —H | —H | —CH$_2$— | 2.79 | |
| 125 | —H | —H | 2-chloro-4-nitrophenoxy | —H | —H | —CH$_2$— | 2.63 | |
| 126 | —CH$_3$ | —H | —CH$_3$ | —CH$_3$ | —H | —CH$_2$— | 3.33 | |
| 127 | —H | —H | —H | —H | —H | —CH$_2$— | 2.65 | |
| 128 | —NO$_2$ | —H | —H | —H | —H | —CH$_2$— | 1.84 | |
| 129 | O-i-propyl | —H | —H | —H | —H | —CH$_2$— | 2.7 | |
| 130 | O=C(—CH=CH—CH=CH—Ph)— | —H | —H | —H | —H | —CH$_2$— | 2.91 | |
| 131 | —CF$_3$ | —H | —H | —H | —H | —CH$_2$— | 2.49 | |
| 132 | —OCF$_3$ | —H | —CF$_3$ | —H | —H | —CH$_2$— | 2.64 | |
| 133 | —H | —OCF$_3$ | —H | —H | —H | —CH$_2$— | 2.63 | |
| 134 | —H | —H | —S—CF$_3$ | —H | —H | —CH$_2$— | 2.35 | |
| 135 | —O—CH$_3$ | —H | —H | —H | —H | —CH$_2$— | 3.07 | |
| 136 | —H | —CH$_3$ | —NH$_2$ | —H | —H | —CH$_2$— | 2.02 | |
| 137 | —H | —Cl | —H | —H | —H | —CH$_2$— | 0.83 | |
| 138 | 2,4-dichlorophenoxy | —H | —H | —CH$_3$ | —H | ᵃ⁾CH$_2$— ᵇ⁾CH(C$_6$H$_5$) | | 159 |
| 139 | —Cl | —H | —H | —H | —H | | | |

The bonds referred to by * show the bonding positions
The carbon atoms referred to by ᵃ⁾ in group Y are linked to the SO$_2$ group, while the carbon atoms referred to by ᵇ⁾ are linked to the S group.
The logP values were determined as per EEC Directive 79/831 Annex V. A8 by HPLC (gradient method, acetonitrile/0.1% aqueous phosphoric acid)

TABLE 2

| Ex. No. | Structural formula | logP | m.p. (° C.) |
|---|---|---|---|
| 140 | | | |
| 141 | | 2.64 | |
| 142 | | 1.9 | |
| 143 | | 0.48 | |
| 144 | | 2.65 | |
| 145 | | | |

TABLE 2-continued

| Ex. No. | Structural formula | logP | m.p. (° C.) |
|---|---|---|---|
| 146 | | 3.43 | |
| 147 | | 2.77 | |
| 148 | | 1.92 | |
| 149 | | 1.55 | |
| 150 | | 2.6 | |
| 151 | | 2.31 | |

TABLE 2-continued

| Ex. No. | Structural formula | logP | m.p. (° C.) |
|---|---|---|---|
| 152 | | 2.52 | |
| 153 | | 3.31 | |
| 154 | | 1.93 | |
| 155 | | 1.86 | |
| 156 | | | 175 |
| 157 | | 2.8 | |

TABLE 2-continued

| Ex. No. | Structural formula | logP | m.p. (° C.) |
|---|---|---|---|
| 158 | | 2.66 | |

Preparation of the Starting Materials of the Formula (II)

EXAMPLE (II -1)

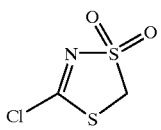

4.3 g (24.5 mmol) of 3-methylthio-1,4,2-dithiazole 1,1-dioxide are added in the course of 10 minutes to 17 g (122 mmol) of sulphuryl chloride. The mixture is heated to 40° C. and stirred for 24 hours at this temperature. After the excess sulphuryl chloride has been evaporated in vacuo, the residue is stirred with diethyl ether, filtered off with suction and dried in vacuo. This gives 3.3 g (78% of theory) of 3-chloro-1,4,2-dithiazole 1,1-dioxide.

$^1$H NMR (CDCl$_3$): δ=4.67 ppm.

The novel intermediates of the formula (II-a) stated in Table 3 were also obtained analogously:

TABLE 3

| Ex. | Structural formula | logP |
|---|---|---|
| (II-a-1) | | 2.63 |
| (II-a-2) | | 2.75 |

Preparation of the Starting Materials of the Formula (IV)

The starting materials of the formula (IV) were prepared analogously to the protocol in U.S. Pat. No. 3,345,374. The following compounds, some of which are new, were obtained analogously:

TABLE 4

| Ex. No. | Structural formula | logP | m.p. (° C.) | Note |
|---|---|---|---|---|
| (IV-1) | | | 129 | known |
| (IV-2) | | | 160 | known |
| (IV-3) | | 1.38 | | |
| (IV-4) | | 2.80 | | |
| (IV-5) | | 2.65 | | |
| (IV-6) | | 2.54 | | |

Use Examples
EXAMPLE A

To confirm the activity against fungi (*Penicillium brevicaule, Chaetomium globosum, Aspergillus Niger*), the minimum inhibitory concentrations (MICs) of agents according to the invention are determined:

Active compounds according to the invention are added in concentrations of from 0.1 mg/l to 5 000 mg/l to an agar prepared using malt extract. After the agar has solidified, it is contaminated with pure-bred cultures of the test organisms listed in Table 2. After storage for 2 weeks at 28° C. and a relative atmospheric humidity of 60 to 70%, the MIC is determined. The MIC is the lowest concentration of active compound at which no growth whatsoever by the microbial species used occurs; it is indicated in the table which follows.

For the fungi *Penicillium brevicaule, Chaetomium globosum, Aspergillus Niger,* the compounds (1), (92), (93), (94) and (100) show MIC values of 10–100 ppm.

TABLE A

Minimum inhibitory concentrations (ppm) of compounds of the formula (I) according to the invention

| Active compound according to the invention | Penicillium brevicaule | Chaetomium globosum | Aspergillus Niger |
|---|---|---|---|
| 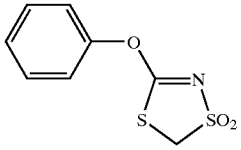 (92) | 100 | 100 | 100 |
| 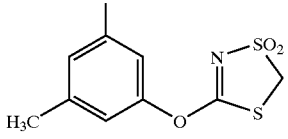 (1) | 20 | 100 | 100 |
| 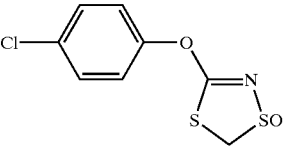 (93) | 20 | 50 | 100 |
| 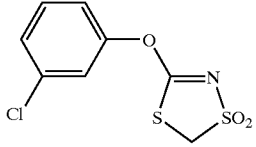 (94) | 20 | 100 | 100 |

TABLE A-continued

Minimum inhibitory concentrations (ppm) of compounds of the formula (I) according to the invention

| Active compound according to the invention | Penicillium brevicaule | Chaetomium globosum | Aspergillus Niger |
|---|---|---|---|
| 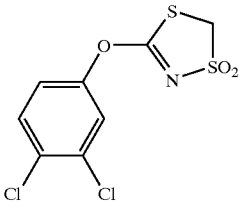 (100) | 20 | 50 | 100 |

EXAMPLE B

Plasmopara Test (Grapevine)/Protective

Solvent: 47 parts by weight of acetone

Emulsifier: 3 parts by weight of alkylaryl polyglycol ether

To prepare a suitable active compound preparation, 1 part by weight of active compound is mixed with the stated amounts of solvent and emulsifier, and the concentrate is diluted with water to the desired concentration.

To test for protective activity, young plants are sprayed with the active compound preparation at the application rate stated. After the spray coating has dried on, the plants are inoculated with an aqueous spore suspension of *Plasmopara viticola* and then remain for 1 day in an incubation cabinet at approx. 20° C. and a relative atmospheric humidity of 100%. The plants are subsequently placed in a greenhouse for 5 days at approx. 21° C. and approx. 90% relative atmospheric humidity. The plants are then moistened and placed in an incubation cabinet for 1 day.

The test is evaluated 6 days after the inoculation. 0% means an efficacy which corresponds to that of the control, while an efficacy of 100% means that no disease is observed.

In this test, the substances according to the invention mentioned in Examples (14), (21), (27), (28), (40), (41), (42), (141), (1), (95), (96), (98), (99), (100), (101), (102), (105), (106), (119) and (128) show an efficacy of 90% or more at an application rate of 250 g/ha.

TABLE B

Plasmopara test (grapevine)/protective

| Active compound | Application rate of active compound in g/ha | Efficacy in % |
|---|---|---|
| 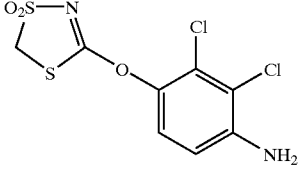 (14) | 250 | 100 |

TABLE B-continued

Plasmopara test (grapevine)/protective

| Active compound | Application rate of active compound in g/ha | Efficacy in % |
|---|---|---|
| (21) | 250 | 95 |
| (27) | 250 | 100 |
| (28) | 250 | 100 |
| (40) | 250 | 95 |
| (41) | 250 | 100 |
| (42) | 250 | 100 |
| (141) | 250 | 99 |
| (1) | 250 | 96 |
| (95) | 250 | 100 |
| (96) | 250 | 100 |
| (98) | 250 | 91 |

TABLE B-continued

Plasmopara test (grapevine)/protective

| Active compound | Application rate of active compound in g/ha | Efficacy in % |
|---|---|---|
| (99) | 250 | 95 |
| (100) | 250 | 100 |
| (101) | 250 | 97 |
| (102) | 250 | 100 |
| (105) | 250 | 100 |
| (106) | 250 | 92 |
| (119) | 250 | 91 |
| (128) | 250 | 94 |

EXAMPLE C

Venturia Test (Apple)/Protective

Solvent: 47 parts by weight of acetone
Emulsifier: 3 parts by weight of alkylaryl polyglycol ether To prepare a suitable active compound preparation, 1 part by weight of active compound is mixed with the stated amounts of solvent and emulsifier, and the concentrate is diluted with water to the desired concentration.

To test for protective activity, young plants are sprayed with the active compound preparation at the application rate stated. After the spray coating has dried on, the plants are inoculated with an aqueous conidial suspension of the apple scab pathogen *Venturia inaequalis* and then remain for 1 day in an incubation cabinet at approx. 20° C. and 100% relative atmospheric humidity.

The plants are then placed into a greenhouse at approx. 21° C. and a relative atmospheric humidity of approx. 90%.

The test is evaluated 12 days after the inoculation. 0% means an efficacy which corresponds to that of the control, while an efficacy of 100% means that no disease is observed.

In this test, the substances according to the invention mentioned in Examples (24), (27), (28), (40), (141), (1), (94), (95), (96), (100), (101), (105), (106), (108), (110), (111), (114), (115) and (133) show an efficacy of 90% or more at an application rate of 250 g/ha.

TABLE C

Venturia test (apple)/protective

| Active compound according to the invention | Application rate of active compound in g/ha | Efficacy in % |
|---|---|---|
| (24) | 250 | 94 |
| (27) | 250 | 98 |
| (28) | 250 | 92 |
| (40) | 250 | 94 |
| (141) | 250 | (90) |
| (1) | 250 | 99 |

TABLE C-continued

Venturia test (apple)/protective

| Active compound according to the invention | Application rate of active compound in g/ha | Efficacy in % |
|---|---|---|
| (94) | 250 | 98 |
| (95) | 250 | 99 |
| (96) | 250 | 95 |
| (100) | 250 | 96 |
| (101) | 250 | 97 |
| (105) | 250 | 98 |
| (106) | 250 | 100 |

TABLE C-continued

Venturia test (apple)/protective

| Active compound according to the invention | Application rate of active compound in g/ha | Efficacy in % |
|---|---|---|
| 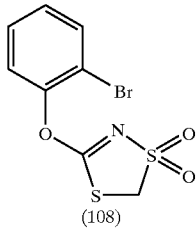 (108) | 250 | 92 |
| 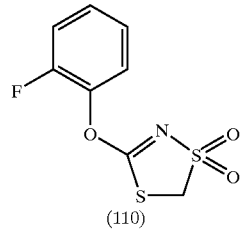 (110) | 250 | 94 |
| 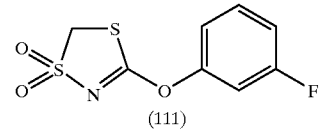 (111) | 250 | 100 |
| 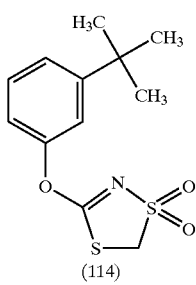 (114) | 250 | 93 |
| 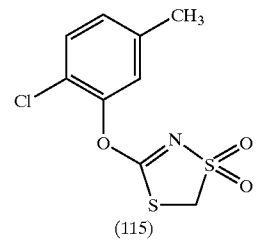 (115) | 250 | 100 |
| 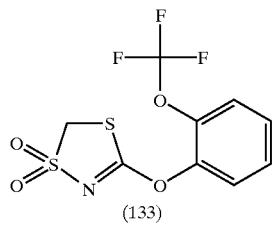 (133) | 250 | 100 |

EXAMPLE D

Phytophthora Test (Tomato)/Protective

Solvent: 50 parts by weight of N,N-dimethylformamide
Emulsifier: 1.17 parts by weight of alkylaryl polyglycol ether To prepare a suitable active compound preparation, 1 part by weight of active compound is mixed with the stated amounts of solvent and emulsifier, and the concentrate is diluted with water to the desired concentration.

To test for protective activity, young plants are sprayed with the active compound preparation at the application rate stated. 1 day after the treatment, the plants are inoculated with a spore suspension of *Phytiphthora infestans*. The plants are subsequently placed into a controlled-environment cell at approximately 96% relative atmospheric humidity and a temperature of approx. 20° C.

The test is evaluated 7 days after the inoculation. 0% means an efficacy which corresponds to that of the control, while an efficacy of 100% means that no disease is observed.

In this test, the substances according to the invention mentioned in Examples (26), (127), (128), (133) and (13) show an efficacy of 90% or more at an application rate of 750 g/ha.

TABLE D

Phytophthora test (tomato)/protective

| Active compound according to the invention | Application rate of active compound in g/ha | Efficacy in % |
|---|---|---|
| 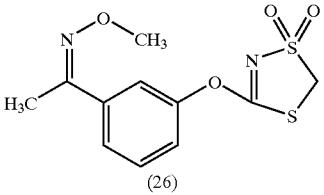 (26) | 750 | 90 |
| 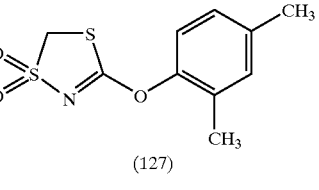 (127) | 750 | 90 |
| 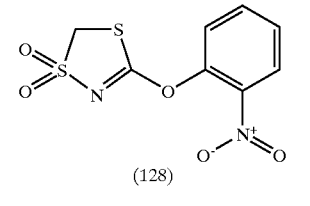 (128) | 750 | 90 |
| 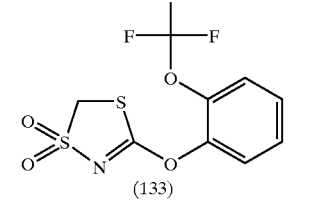 (133) | 750 | 95 |

TABLE D-continued

Phytophthora test (tomato)/protective

| Active compound according to the invention | Application rate of active compound in g/ha | Efficacy in % |
|---|---|---|
| (13) [structure: chloro-methyl propanamide linked to dichlorophenoxy-thiazoline-S-oxide] | 750 | 95 |

EXAMPLE E

Myzus Test

Solvent: 6 parts by weight of dimethylformamide
67 parts by weight of methanol
Emulsifier: 2 parts by weight of alkylaryl polyglcol ether To prepare a suitable active compound preparation, 1 part by weight of active compound is mixed with the stated amount of solvent and the stated amount of emulsifier, and the concentrate is diluted with emulsifier-containing water to the desired concentrations.

Field bean (*Vicia faba*) seedlings which are infested with the green peach aphid (*Myzus persicae*) are immersed into an active compound preparation of the desired concentration and placed into a plastic box.

After the desired period of time, the destruction is determined in %. 100% means that all the animals have been killed; 0% means that none of the animals have been killed.

In this test, a destruction of 90% or more is shown for example by the following compounds of the preparation examples (22) and (40).

TABLE E

Plant-injurious insects
Myzus test

| Active compound according to the invention | Active compound concentration in % | Destruction in % after 6$^d$ |
|---|---|---|
| (22) [structure] | 0.01 | 100 |

TABLE E-continued

Plant-injurious insects
Myzus test

| Active compound according to the invention | Active compound concentration in % | Destruction in % after 6$^d$ |
|---|---|---|
| (40) [structure] | 0.01 | 90 |

EXAMPLE F

Plutella Test/Synthetic Feed

Solvent: 100 parts by weight of acetone
Emulsifier: 1900 parts by weight of methanol To prepare a suitable active compound preparation, 1 part by weight of active compound is mixed with the stated amount of solvent and the concentrate is diluted with methanol to the desired concentration.

A stated amount of active compound preparation of the desired concentration is pipetted onto a standardized amount of synthetic feed. After the methanol has evaporated, the lid of a film box, populated with approx. 100 Plutella eggs, is placed over each cavity. The freshly hatched larvae crawl onto the treated synthetic feed.

After the desired time, the destruction is determined in %. 100% means that all the animals have been killed; 0% means that none of the animals have been killed.

In this test, a destruction of 95% after 7 days is caused, for example, by the compounds of preparation examples (14) at an exemplary active compound concentration of 0.1%.

TABLE F

Plant-injurious insects
Plutella test/synthetic feed

| Active compound | Active compound concentration in % | Destruction in % after 7$^d$ |
|---|---|---|
| (12) [structure] | 0.1 | 95 |

EXAMPLE G

Tetranychus Test (OP-resistant/Immersion Treatment)

Solvent: 3 parts by weight of dimethylformamide
Emulsifier: 1 part by weight of alkylaryl polyglycol ether To prepare a suitable active compound preparation, 1 part by weight of active compound is mixed with the stated amount of solvent and the stated amount of emulsifier, and the concentrate is diluted with water to the desired concentrations.

Bean plants (*Phaseolus vulgaris*) which are severely infested by all stages of the greenhouse red spider mite (*Tetranychus urticae*) are immersed into an active compound preparation of the desired concentration.

After the desired time, the efficacy is determined in %. 100% means that all the spider mites have been killed; 0% means that none of the spider mites have been killed.

In this test, a destruction of 95% is shown, after 7 days, for example by the compound of preparation examples (20) at an exemplary active compound concentration of 0.01%.

TABLE G

Plant-injurious insects
Tetranychus test (OP-resistant/immersion treatment)

| Active compound | Active compound concentration in % | Destruction in % after 7$^h$ |
|---|---|---|
| 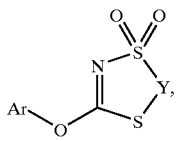 (20) | 0.01 | 95 |

What is claimed is:
1. A compound of the formula (I),

(I)

wherein
Ar represents substituted or unsubstituted aryl and
Y represents substituted or unsubstituted, straight-chain or branched alkanediyl.
2. A compound of the formula (I) according to claim 1, wherein
Ar represents unsubstituted or substituted phenyl, substituents for phenyl being the following:
halogen, cyano, thiocyano, nitro, amino, formyl, carbamoyl, thiocarbamoyl, hydrogen, hydroxyl;
in each case straight-chain or branched alkyl, cyanoalkyl, hydroxyalkyl, alkoxy, alkoxyalkyl, hydroxyalkoxy, alkylthioalkyl, alkylaminoalkyl, dialkylaminoalkyl, alkylthio, alkylsulphinyl or alkylsulphonyl, each of which has 1 to 8 carbon atoms;
in each case straight-chain or branched alkenyl, alkenyloxy or alkenylcarbonyl, each of which has 2 to 6 carbon atoms in the alkenyl moiety and each of which is optionally monosubstituted or disubstituted by cyano, nitro, phenyl, nitrophenyl, dinitrophenyl, alkoxycarbonylamino, phthalimidyl, bis-(alkoxycarbonylamino) or dioxobenzimidazolyl;
in each case straight-chain or branched halogenoalkyl, halogenoalkoxy, halogenoalkylthio, halogenoalkyl-sulphinyl or halogenoalkylsulphonyl, each of which has 1 to 6 carbon atoms and 1 to 13 identical or different halogen atoms;
in each case straight-chain or branched halogenoalkenyl or halogenoalkenyloxy, each of which has 2 to 6 carbon atoms and 1 to 11 identical or different halogen atoms;
in each case straight-chain or branched alkylamino, dialkylamino, alkylcarbonyl, thiocyanoalkylcarbonyl, halogenoalkylcarbonyl (having 1 to 3 halogen atoms), alkoxycarbonyl, alkoxycarbonylazoalkyl, alkylaminocarbonyl, dialkylaminocarbonyl or arylalkylaminocarbonyl having 1 to 6 carbon atoms in the respective hydrocarbon chains, or cycloalkylcarbonylamino or cycloalkyl, each of which has 3 to 6 carbon atoms in the cycloalkyl moiety and each of which is optionally monosubstituted to tetrasubstituted by halogen or alkyl having 1 to 4 carbon atoms;
cycloalkyl or cycloalkyloxy, each of which has 3 to 6 carbon atoms;
phenyl, phenoxy, phenylazo, phenylthio, phenylsulphonyl, phenylcarbonyl, phenylalkylcarbonyl, or phenylalkoxy having 1 to 4 carbon atoms in the alkyl moiety, optionally substituted in each case by halogen, alkyl, phenyl, alkoxy, alkylthio, alkylsulphinyl or alkylsulphonyl having 1 to 4 carbon atoms, halogenoalkyl, halogenoalkoxy, halogenoalkylthio, halogenoalkylsulphinyl or halogenoalkylsulphonyl having 1 to 4 carbon atoms and 1 to 9 halogen atoms, heterocyclyl, heterocyclylalkyl having 1 to 4 carbon atoms in the alkyl moiety, heterocyclyloxy, heterocyclylthio, heterocyclylsulphinyl, heterocyclylsulphonyl, heterocyclylcarbonyl, heterocyclylthiocarbonyl, benzoheterocyclyl, benzoheterocyclylalkyl having 1 to 4 carbon atoms in the alkyl moiety, benzoheterocyclyloxy, benzoheterocyclylthio, benzoheterocyclylsulphinyl, benzoheterocyclylsulphonyl, benzoheterocyclylcarbonyl or benzoheterocyclylthiocarbonyl, each of which has 5 or 6 ring members in the heterocyclyl moiety, in each case optionally substituted by halogen, oxo, alkyl, alkoxy, alkylthio, alkylsulphinyl or alkylsulphonyl having 1 to 4 carbon atoms, halogenoalkyl, halogenoalkoxy, halogenoalkylthio, halogenoalkylsulphinyl or halogenoalkylsulphonyl having 1 to 4 carbon atoms and 1 to 9 halogen atoms or phenyl, or a group

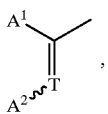

where
T represents CH or nitrogen,
$A^1$ represents hydrogen or alkyl having 1 to 4 carbon atoms, cycloalkyl having 3 to 6 carbon atoms, phenyl, heterocyclyl having 5 or 6 ring members, alkoxycarbonyl having 1 to 4 carbon atoms in the alkyl moiety, benzylaminocarbonyl, benzyloxyaminocarbonyl or aminocarbonyl, and
$A^2$ represents hydroxyl, amino, alkyl, phenyl, benzyl, alkoxy, cyanoalkoxy, benzyloxy, alkylamino, dialkylamino, alkoxycarbonylamino, alkoxycarbonylphenyl, in each case with 1 to 4 carbon atoms in the respective alkyl chains, or alkenyloxy having 2 to 4 carbon atoms, or Ar represents one of the following groups:

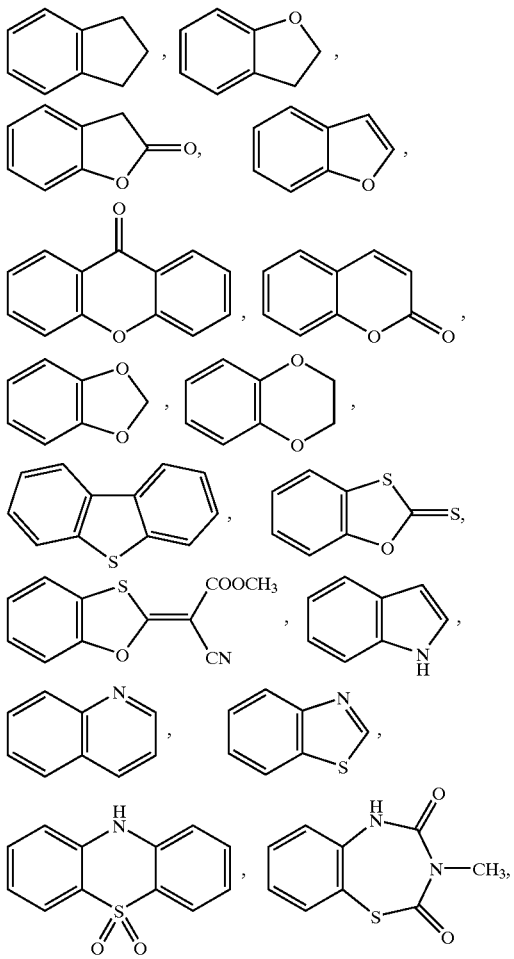

each of which is bonded via the phenyl ring and each of which can, in turn, be monosubstituted to hexasubstituted, the substituents being selected amongst the following list:

halogen, cyano, thiocyano, nitro, amino, formyl, carboxyl, carbamoyl, thiocarbamoyl;

in each case straight-chain or branched alkyl, alkoxy, alkylthio, alkylsulphinyl or alkylsulphonyl, each of which has 1 to 8 carbon atoms;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

in each case straight-chain or branched alkylamino, dialkylamino, alkylcarbonyl, alkoxycarbonyl, alkylaminocarbonyl, dialkylaminocarbonyl or arylalkylaminocarbonyl having 1 to 6 carbon atoms in the respective hydrocarbon chains or cycloalkylcarbonylamino or cycloalkyl having 3 to 6 carbon atoms in the cycloalkyl moiety, in each case monosubstituted to tetrasubstituted by halogen or alkyl having 1 to 4 carbon atoms;

cycloalkyl or cycloalkyloxy, each of which has 3 to 6 carbon atoms;

phenyl, phenoxy, phenylthio, phenylsulphonyl, phenylcarbonyl, phenylalkylcarbonyl, or phenylalkoxy having 1 to 4 carbon atoms in the alkyl moiety, in each case optionally substituted by nitro, halogen, alkyl, phenyl, alkoxy, alkylthio, alkylsulphinyl or alkylsulphonyl having 1 to 4 carbon atoms, halogenoalkyl, halogenoalkoxy, halogenoalkylthio, halogenoalkylsulphinyl or halogenoalkylsulphonyl having 1 to 4 carbon atoms and 1 to 9 halogen atoms, and Y represents alkylene having 1 to 8 carbon atoms which is optionally monosubstituted or disubstituted by phenyl, the linkage sites of the alkylene chain being at the same or at directly adjacent carbon atoms.

3. A compound of the formula (I-a),

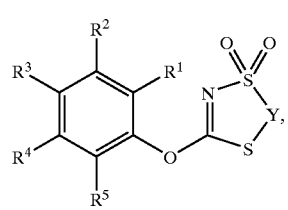

(I-a)

wherein $R^1$, $R^2$, $R^3$, $R^4$ and $R^5$ are identical or different and independently of one another represent the following substituents:

halogen, cyano, thiocyano, nitro, amino, formyl, carbamoyl, thiocarbamoyl, hydrogen, hydroxyl;

in each case straight-chain or branched alkyl, cyanoalkyl, hydroxyalkyl, alkoxy, alkoxyalkyl, hydroxyalkoxy, alkylthioalkyl, alkylaminoalkyl, dialkylaminoalkyl, alkylthio, alkylsulphinyl or alkylsulphonyl, each of which has 1 to 8 carbon atoms;

in each case straight-chain or branched alkenyl, alkenyloxy or alkenylcarbonyl, each of which has 2 to 6 carbon atoms in the alkenyl moiety and each of which is optionally monosubstituted or disubstituted by cyano, nitro, phenyl, nitrophenyl, dinitrophenyl, alkoxycarbonylamino, phthalimidyl, bis-(alkoxycarbonylamino) or dioxobenzimidazolyl;

in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

in each case straight-chain or branched halogenoalkenyl or halogenoalkenyloxy, each of which has 2 to 6 carbon atoms and 1 to 11 identical or different halogen atoms;

in each case straight-chain or branched alkylamino, dialkylamino, alkylcarbonyl, thiocyanoalkylcarbonyl, halogenoalkylcarbonyl (having 1 to 3 halogen atoms), alkoxycarbonyl, alkoxycarbonylazoalkyl, alkylaminocarbonyl, dialkylaminocarbonyl or arylalkylaminocarbonyl having 1 to 6 carbon atoms in the respective hydrocarbon chains, or cycloalkylcarbonylamino or cycloalkyl having 3 to 6 carbon atoms in the cycloalkyl moiety, each of which is optionally monosubstituted to tetrasubstituted by halogen or alkyl having 1 to 4 carbon atoms;

cycloalkyl or cycloalkyloxy, each of which has 3 to 6 carbon atoms;
phenyl, phenoxy, phenylazo, phenylthio, phenylsulphonyl, phenylcarbonyl, phenylalkylcarbonyl, or phenylalkoxy having 1 to 4 carbon atoms in the alkyl moiety, in each case optionally substituted by halogen, alkyl, phenyl, alkoxy, alkylthio, alkylsulphinyl or alkylsulphonyl having 1 to 4 carbon atoms, halogenoalkyl, halogenoalkoxy, halogenoalkylthio, halogenoalkylsulphinyl or halogenoalkylsulphonyl having 1 to 4 carbon atoms and 1 to 9 halogen atoms, heterocyclyl, heterocyclylalkyl having 1 to 4 carbon atoms in the alkyl moiety, heterocyclyloxy, heterocyclylthio, heterocyclylsulphinyl, heterocyclylsulphonyl, heterocyclylcarbonyl, heterocyclylthiocarbonyl, benzoheterocyclyl, benzoheterocyclylalkyl having 1 to 4 carbon atoms in the alkyl moiety, benzoheterocyclyloxy, benzoheterocyclylthio, benzoheterocyclylsulphinyl, benzoheterocyclylsulphonyl, benzoheterocyclylcarbonyl or benzoheterocyclylthiocarbonyl, each of which has 5 or 6 ring members in the heterocyclyl moiety, in each case optionally substituted by halogen, oxo, alkyl, alkoxy, alkylthio, alkylsulphinyl or alkylsulphonyl having 1 to 4 carbon atoms, halogenoalkyl, halogenoalkoxy, halogenoalkylthio, halogenoalkylsulphinyl or halogenoalkylsulphonyl having 1 to 4 carbon atoms and 1 to 9 halogen atoms or phenyl, or a group

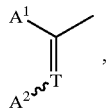

where
T represents CH or nitrogen,
$A^1$ represents hydrogen or alkyl having 1 to 4 carbon atoms, cycloalkyl having 3 to 6 carbon atoms, phenyl, heterocyclyl having 5 or 6 ring members, alkoxycarbonyl having 1 to 4 carbon atoms in the alkyl moiety, benzylaminocarbonyl, benzyloxyaminocarbonyl or aminocarbonyl,
$A^2$ represents hydroxyl, amino, alkyl, phenyl, benzyl, alkoxy, cyanoalkoxy, benzyloxy, alkylamino, dialkylamino, alkoxycarbonylamino, alkoxycarbonylphenyl, each of which has 1 to 4 carbon atoms in the respective alkyl chains, or alkenyloxy having 2 to 4 carbon atoms, and
Y represents alkylene having 1 to 8 carbon atoms which is optionally monosubstituted or disubstitufed by phenyl, the linkage sites of the alkylene chain being at the same or at directly adjacent carbon atoms.

4. A compound of the formula (I-a) according to claim 3, wherein
$R^1$, $R^2$, $R^3$, $R^4$ and $R^5$ are identical or different and independently of one another represent the following substituents:
fluorine, chlorine, bromine, cyano, thiocyano, nitro, amino, formyl, carbamoyl, thiocarbamoyl, hydrogen, hydroxyl, methyl, ethyl, n- or i-propyl, n-, i-, s- or t-butyl, methoxymethyl, cyanomethyl, hydroxymethyl, hydroxyethyl, hydroxypropyl, hydroxybutyl, hydroxypentyl, hydroxyhexyl, methoxy, ethoxy, n- or i-propoxy, hydroxyethoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy, vinylcarbonyl, allylcarbonyl, 2-methylallylcarbonyl, propen-1-ylcarbonyl, crotonylcarbonyl, propargylcarbonyl, each of which is optionally monosubstituted or disubstituted by cyano, nitro, phenyl, nitrophenyl, dinitrophenyl, methoxycarbonylamino, phthalimidyl, bis-(methoxycarbonylamino) or dioxobenzimidazolyl; trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, methylcarbonyl, acetyl, propionyl, thiocyanomethylcarbonyl, chloro-t-butylcarbonyl, methoxycarbonyl, ethoxycarbonyl, ethoxycarbonylazomethyl, methylaminocarbonyl, ethylaminocarbonyl, dimethylaminocarbonyl, diethylaminocarbonyl; or cyclopropyl, cyclopropylcarbonylamino, cyclobutyl, cyclopentyl or cyclohexyl, each of which is optionally monosubstituted to tetrasubstituted by chlorine, bromine, methyl or ethyl;
cyclopentyl, cyclohexyl, cyclopentyloxy, cyclohexyloxy, cyclohexylcarbonylamino, phenyl, phenoxy, phenylazo, phenylthio, phenylsulphonyl, phenylcarbonyl, benzylcarbonyl or benzyl, each of which is optionally substituted by nitro, fluorine, chlorine, methyl, trifluoromethyl, phenyl or methoxy, dithiazole, dithiazoloxy, oxadiazole, benzofuranyl, benzofuranylcarbonyl, pyridazine, benzoxazole, pyrimidyl, morpholinyl, morpholinylthiocarbonyl, thienyl, imidazolyl, thiadiazolyl, pyridyl, pyridazinone, furyl, piperazinyl, pyrimidylthio, thiazolyl, thiazolylthio, benzazothiepine, dioxazinyl, thiadiazolylsulphonyl, each of which is optionally monosubstituted to trisubstituted by methyl, ethyl, n- or i-propyl, n-, i-, s- or t-butyl, oxo, fluorine, chlorine, bromine, trifluoromethyl or phenyl; or a group

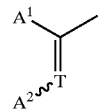

in which
T represents CH or nitrogen,
$A^1$ represents hydrogen, methyl, ethyl, n- or i-propyl, n-, i-, s- or t-butyl, cyclopentyl, cyclohexyl, phenyl, dioxazinyl, methoxycarbonyl, ethoxycarbonyl, benzylaminocarbonyl, benzyloxyaminocarbonyl or aminocarbonyl,
$A^2$ represents hydroxyl, amino, methyl, ethyl, phenyl, benzyl, methoxy, ethoxy, n- or i-propoxy, n-, i-, s- or t-butoxy, cyanomethoxy, benzyloxy, methylamino, ethylamino, dimethylamino, diethylamino, methoxycarbonylamino, ethoxycarbonylamino, methoxycarbonylphenyl, ethoxycarbonylphenyl or allyloxy, and Y represents methylene, 1,1-ethylene, 1,2-ethylene 1,1-, 1,2-,1,3- or 2,2-propylene, 1,1-, 1,2-, 1,3-, 1,4-, 2,2-, 2,3-butylene or 1,1-,1,2- or 1,3-(2-methyl-propylene), each of which is optionally monosubstituted or disubstituted by phenyl.

5. A compound of the formula (I-b),

wherein
Ar$^1$ represents one of the following groups:

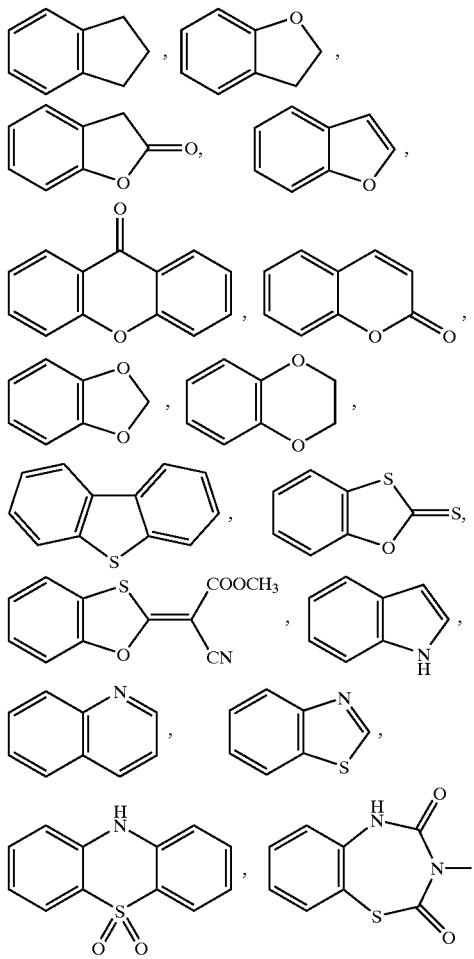

each of which is bonded via the phenyl ring and each of which can, in turn, be monosubstituted to hexasubstituted, the substituents being selected amongst the following list:
halogen, cyano, thiocyano, nitro, amino, formyl, carboxyl, carbamoyl, thiocarbamoyl;
in each case straight-chain or branched alkyl, alkoxy, alkylthio, alkylsulphinyl or alkylsulphonyl, each of which has 1 to 8 carbon atoms;
in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;
in each case straight-chain or branched alkylamino, dialkylamino, alkylcarbonyl, alkoxycarbonyl, alkylaminocarbonyl, dialkylaminocarbonyl or arylalkylaminocarbonyl having 1 to 6 carbon atoms in the respective hydrocarbon chains, or cycloalkylcarbonylamino or cycloalkyl having 3 to 6 carbon atoms in the cycloalkyl moiety and in each case monosubstituted to tetrasubstituted by halogen or alkyl having 1 to 4 carbon atoms;
cycloalkyl or cycloalkyloxy, each of which has 3 to 6 carbon atoms;
phenyl, phenoxy, phenylthio, phenylsulphonyl, phenylcarbonyl, phenylalkylcarbonyl, or phenylalkoxy having 1 to 4 carbon atoms in the alkyl moiety, in each case optionally substituted by nitro, halogen, alkyl, phenyl, alkoxy, alkylthio, alkylsulphinyl or alkylsulphonyl having 1 to 4 carbon atoms, halogenoalkyl, halogenoalkoxy, halogenoalkylthio, halogenoalkylsulphinyl or halogenoalkylsulphonyl having 1 to 4 carbon atoms and 1 to 9 halogen atoms, and Y represents alkylene having 1 to 8 carbon atoms which is optionally monosubstituted or disubstituted by phenyl, the linkage sites of the alkylene chain being at the same or at directly adjacent carbon atoms.

6. A compound of the formula (I-b) according to claim 5, wherein
Ar$^1$ represents one of the following groups:

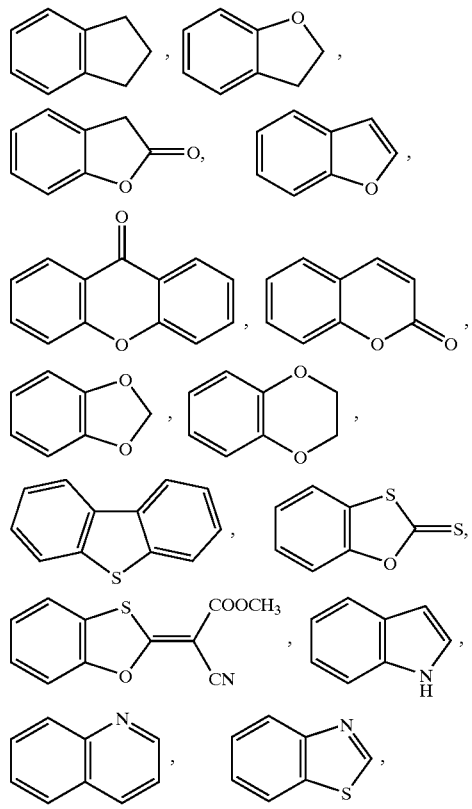

-continued

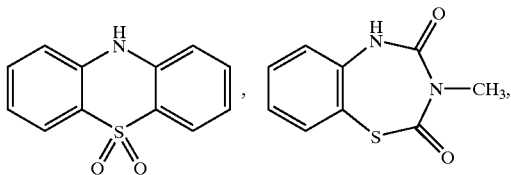

each of which is bonded via the phenyl ring and can, in turn, be monosubstituted to hexasubstituted, the substituents being selected from amongst the following list:

fluorine, chlorine, bromine, cyano, thiocyano, nitro, amino, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl; cyclopropyl, cyclobutyl, cyclopentyl or cyclohexyl, each of which is optionally monosubstituted to tetrasubstituted by chlorine, bromine, methyl or ethyl;

cyclopentyl, cyclohexyl, cyclopentyloxy, cyclohexyloxy, phenyl, phenoxy, phenylthio, phenylsulphonyl, phenylcarbonyl, benzylcarbonyl or benzyl, each of which is optionally substituted by nitro, fluorine, chlorine, methyl, trifluoromethyl, phenyl or methoxy, and Y represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally monosubstituted or disubstituted by phenyl.

7. A compound of the formula (II-a),

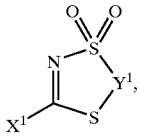

(II-a)

wherein $Y^1$ represents methylene or 1,2-ethylene, each of which is monosubstituted or disubstituted by phenyl, or represents 1,1-ethylene, 1,1-, 1,2- or 2,2-propylene, 1,1-, 1,2-, 2,2-, 2,3-butylene or 1,1- or 1,2-(2-methyl-propylene), each of which is optionally monosubstituted or disubstituted by phenyl, and $X^1$ represents halogen.

8. A composition comprising a compound according to claim 1 and an ingredient selected from extenders, carriers, surfactants and combinations thereof.

9. A method of controlling pests, comprising the step of applying a compound according to claim 1 to pests and/or their environment.

10. A method of controlling pests, comprising the step of applying a composition according to claim 8 to pests and/or their environment.

11. A process for the preparation of a compound of the formula (I) according to claim 1, comprising the step of reacting a compound of the formula (II)

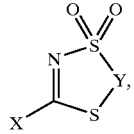

(II)

wherein

Y is as stated in claim 1 and

X represents halogen, alkyl- or arylsulphonyl a phenol of the formula (III),

Ar—OH        (III)

wherein

Ar is as stated in claim 1.

12. A process for the preparation of a compound of the formula (II-a) as defined in claim 7, comprising the step of reacting a compound of the formula (IV)

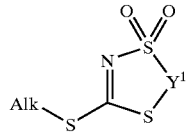

(IV)

wherein $Y^1$ is as stated in claim 7 and

Alk represents alkyl.

13. A process for the preparation of a composition, comprising the step of mixing a compound according to claim 1 with extenders and/or carriers and/or surfactants.

14. A composition comprising a compound according to claim 3 and an ingredient selected from extenders, carriers, surfactants and combinations thereof.

15. A composition comprising a compound according to claim 5 and an ingredient selected from extenders, carriers, surfactants and combinations thereof.

16. A method according to claim 9, wherein the pests are selected from the group consisting of insects, arachnids, nematodes and combinations thereof.

17. A method according to claim 10, wherein the pests are selected from the group consisting of insects, arachnids, nematodes and combinations thereof.

18. A process according to claim 11, wherein the step of reacting the compound of the formula (II) and the phenol of the formula (III) occurs in the presence of an ingredient selected from the group consisting of diluents, acid acceptors, catalysts and combinations thereof.

19. A process according to claim 12, wherein the halogenating agent is selected from the group consisting of chlorine, bromine, iodine, sulphuryl chloride, chlorosuccinimide, bromosuccinimide, 1,3-dibromo-5,5-dimethylhydantoin and iodosuccinimide.

20. A process for the preparation of a composition, comprising the step of mixing a compound according to claim 3 with extenders and/or carriers and/or surfactants.

* * * * *